(12) United States Patent
Clark

(10) Patent No.: US 6,645,739 B2
(45) Date of Patent: Nov. 11, 2003

(54) YEAST EXPRESSION SYSTEMS, METHODS OF PRODUCING POLYPEPTIDES IN YEAST, AND COMPOSITIONS RELATING TO SAME

(75) Inventor: Mike A. Clark, Lexington, KY (US)

(73) Assignee: Phoenix Pharmacologies, Inc., Lexington, KY (US)

( * ) Notice: Subject to any disclaimer, the term of this patent is extended or adjusted under 35 U.S.C. 154(b) by 0 days.

(21) Appl. No.: 09/915,815

(22) Filed: Jul. 26, 2001

(65) Prior Publication Data

US 2003/0092099 A1 May 15, 2003

(51) Int. Cl.$^7$ ............ C12P 21/06; C12N 1/16; C12N 15/63; C07H 21/04
(52) U.S. Cl. ............ 435/69.1; 435/41; 435/69.9; 435/71.1; 435/471; 435/483; 435/243; 435/254.1; 435/255.1; 435/255.3; 435/320.1; 435/254.11; 435/254.2; 536/23.1; 536/24.1
(58) Field of Search ............ 435/41, 69.1, 69.3, 435/69.4, 69.5, 69.51, 69.52, 69.6, 69.8, 69.9, 70.5, 71.1, 471, 476, 477, 481, 483, 320.1, 243, 252.3, 254.1, 255.1, 255.5; 536/22.1, 23.1, 24.1

(56) References Cited

U.S. PATENT DOCUMENTS

| | | | |
|---|---|---|---|
| 4,414,329 A | 11/1983 | Wegner | |
| 4,615,974 A | 10/1986 | Kingsman et al. | |
| 4,808,537 A | 2/1989 | Stroman et al. | |
| 4,855,231 A | 8/1989 | Stroman et al. | |
| 5,002,876 A | 3/1991 | Sreekrishna et al. | |
| 5,641,661 A | 6/1997 | Kumagai et al. | |
| 5,707,828 A | * 1/1998 | Sreekrishna et al. | 435/59.1 |
| 5,804,183 A | * 9/1998 | Filpula et al. | 424/94.6 |
| 5,849,524 A | * 12/1998 | Kondo et al. | 435/69.1 |
| 6,258,559 B1 | * 7/2001 | Zamost | 435/69.1 |

FOREIGN PATENT DOCUMENTS

EP 0 299 108 A1 1/1989

OTHER PUBLICATIONS

Beggs, J.D. "Transformation of yeast by a replicating hybrid plasmid", *Nature*, 1978, 275, pp 104–108.
Bogdanova, A.I. et al., "Plasmid reorganization during integrative transformation in Hansenula polymorpha", *Yeast*, 1995, 11, pp 343–353.
Cregg, J.M. et al., "Pichia pastoris as a host system for transformations", *Mol Cell Biol.*, 1985, 5, pp 3376–3385.
Cregg, J.M. et al., "Recent advances in the expression of foreign genes in pichia pastoris", *Bio/Technology*, 1993, 11, pp 905–910.
Didion, T. et al., "Targeting signal of the peroxisomal catalase in the methylotrophic yeast Hansenula polymorpha", *FEBS*, 1992, 303(2,3), pp 113–116.
Dohmen, R.J. et al., "An efficient transformation procedure enabling long–term storage of competent cells of various yeast genera", *Yeast*, 1991, 7, pp 691–692.
Faber, K.N. et al., "Highly–efficient electrotransformation of the yeast Hansenula polymorpha", *Curr Genet*, 1994, 25, pp 305–310.
Faber, K.N. et al., "Review: Methylotrophic yeasts as factories for the production of foreign proteins", *Yeast*, 1995, 11, pp 1331–1344.
Hiep, T.T. et al., "Transformation in the methylotrophic yeast pichia methanolica utilizing homologous ADE1 and heterologous *saccharomyces cerevisiae* ADE2 and LEU2 genes as genetic markers", *Yeast*, 1993, 9, pp 1189–1197.
Janowicz, Z.A. et al., "Cloning and characterization of the DAS gene encoding the major methanol assimilatory enzyme from the methylotrophic yeast *Hansenula polymorpha*", *Nuc Acids Res*, 1985, 13(9), pp 3043–3063.
Klebe, R.J. et al., "A general method for polyethylene–glycol–induced genetic transformation of bacteria and yeast", *Gene*, 1983, 25, pp 333–341.
Needleman, S.B. et al., "A general method applicable to the search for similarities in the amino acid sequence of two proteins", *J. Mol. Biol.*, 1970, 48, pp 443–453.
Romanos, M., "Advances in the use of pichia pastoris for high–level gene expression", *Curr. Opin. Biotech.*, 1995, 6, pp 527–533.
Romanos, M. et al., Foreign gene expression in yeast: a review, *Yeast*, 1992, 8, pp 423–488.
Scorer, C.A. et al., "Rapid selection using G418 of high copy number transformants of pichia pastoris for high–level foreign gene expression", *Bio/Technology*, 1994, 12, pp 181–184.
Smith T.F. et al., "Comparasion of biosequences", *Adv. Appl. Math.*, 1981, 2, pp 482–489.
Yamada, Y, et al., The phylogentic relationships of methanol–assimilating yeasts based on the partial sequences of 18S and 26S ribosomal RNAs: the proposal of komagatella gen. Nov. (*Saccharomycetaceae*), *Biosci.Biotech.Biochem.*, 1995, 59(3), pp 439–444.

* cited by examiner

Primary Examiner—David Guzo
Assistant Examiner—David A. Lambertson
(74) Attorney, Agent, or Firm—Woodcock Washburn LLP

(57) ABSTRACT

The present invention provides novel expression systems for producing desired polypeptides in certain strains of yeast. The present invention further provides methods for producing polypeptide products using such expression systems. The present invention also provides compositions relating to the same.

13 Claims, 3 Drawing Sheets

YEAST EXPRESSION SYSTEMS, METHODS OF PRODUCING POLYPEPTIDES IN YEAST, AND COMPOSITIONS RELATING TO SAME

FIELD OF THE INVENTION

The present invention relates to expression systems for the production of polypeptides in yeast, to components thereof, and methods of making and using the same.

BACKGROUND OF THE INVENTION

The development of recombinant DNA technology has made possible the production of an enormous variety of useful polypeptides using microorganisms. For example, eukaryotic polypeptides such as human growth hormone, leukocyte interferons, human insulin and human proinsulin have been produced by various microorganisms including bacteria and a variety of yeasts. It is expected that the future will bring the production of polypeptides from a variety of other microorganisms through such recombinant DNA techniques.

Traditionally, commercial efforts employing recombinant DNA technology for the production of polypeptides have focused on the use of *Escherichia coli* (*E. coli*) as a host organism. However, *E. coli* has proved to be an unsuitable host in many situations. For example, *E. coli* contains a number of toxic pyrogenic factors that must be eliminated from any polypeptide to be used as a pharmaceutical product. The efficiency with which this purification can be achieved varies, of course, with the particular polypeptide. In addition, the proteolytic activities of *E. coli* can seriously limit yields of some useful products. These and other considerations have led to increased interest in alternative hosts, in particular, the use of eukaryotic organisms for the production of polypeptide products.

The production of polypeptide products in eukaryotic systems, e.g., yeast, provides for significant advantages relative to the use of prokaryotic systems such as *E. coli* for the production of polypeptides. For example, yeast have been employed in large scale fermentations for centuries, as compared to the relatively recent advent of large scale *E. coli* fermentations. Yeast can generally be grown to higher cell densities than bacteria and are readily adaptable to continuous fermentation processing. U.S. Pat. No. 4,414,329 discusses the growth of yeast such as *Pichia pastoris* (*P. pastoris*) to ultra-high cell densities, i.e., cell densities in excess of 100 g/L. U.S. Pat. No. 5,002,876 discusses the production of human tumor necrosis factor is *P. pastoris*. Yeast hosts are also advantageous in that many critical functions of the organism, e.g., oxidative phosphorylation, are performed within organelles, and hence not exposed to the possible deleterious effects of the organism's production of polypeptides foreign to the wild-type host cells. In addition, as an eukaryotic organism, yeast may prove capable of glycosylating expressed polypeptide products where such glycosylation is important to the bioactivity of the polypeptide product. It is also possible that as a eukaryotic organism, yeast will exhibit the same codon preferences as higher organisms, thus tending toward more efficient production of expression products from mammalian genes or from complementary DNA obtained by reverse transcription from, for example, mammalian messenger RNA ("mRNA").

Methanol assimilating yeasts have been identified as attractive candidates for use in recombinant expression systems. Methanol assimilating yeasts are able to utilize methanol as a source of carbon and energy and can provide several advantages when used in expression systems. For example, some methanol assimilating yeasts grow rapidly on minimal defined media. In addition, certain genes of these yeast are tightly regulated and highly expressed under induced or de-repressed conditions, suggesting that promoters of these genes might be useful for the production of polypeptides of commercial value. Faber et al., Yeast 11:1331 (1995); Cregg et al, Bio/Technology 11:905 (1993), the disclosures of which are hereby incorporated by reference herein in their entirety.

Yeasts having the biochemical pathways necessary for methanol assimilation have traditionally been classified in four genera: Hansenula, Pichia, Candida and Torulopsis. Expression systems have been described using *P. pastoris* and *Hansenula polymorpha*. Faber et al., Curr. Genet. 25:305–10 (1994); Cregg et al., supra; Romanos et al., Yeast 2:423 (1992), the disclosures of which are hereby incorporated by reference herein in their entirety. However, these genera are based on cell morphology and growth characteristics, and do not reflect close genetic relationships. Moreover, it has been shown that not all species within these genera are capable of utilizing methanol as a source of carbon and energy. In addition, an examination of the phylogenetic relationship of several methanol-assimilating yeasts by partial sequencing of 18S and 26S ribosomal RNAs has shown that *Pichia pastoris* has significant base differences from other species of Pichia. See Yamada et al., Biosci. Biotech. Biochem. 59(3):439–44 (1995), the disclosure of which is hereby incorporated by reference herein in its entirety. There may thus be substantial differences in physiology and metabolism between individual species of a genus, indicating that even members of the same genus may have differing characteristics not easily predictable based on phylogenetic characteristics.

The development of these poorly characterized yeast species for use in expression systems has been severely hampered by the lack of knowledge about transformation techniques and conditions, especially the particular regulatory regions for each strain. Depending on the strain of yeast used and the specific transformation technique, from about 50 to about 100,000 transformants per microgram of plasmid are obtained (See, Dohmen et al., Yeast 7, 691–2 (1991). Although *Saccharomyces cervisiae* and *Candida boidinii* can be transformed using lithium acetate, this method does not work well in *Pichia pastoris*. Furthermore, even using the same strain of yeast and the same transformation method, different plasmids yield different efficiencies. Development has also been slowed in part by a lack of suitable materials such as vectors, promoters, selectable markers and host cells. In addition, it has been shown that auxotrophic mutations are often not available, precluding direct selection for transformants by auxotrophic complementation. For recombinant DNA technology to fully sustain its promise, new host/vector systems must be devised which facilitate the manipulation of DNA as well as optimize expression of inserted DNA sequences so that the desired polypeptide products can be prepared under controlled conditions and in high yield.

There is a need for novel expression systems that include certain strains of yeast as hosts for the production of polypeptide products. The present invention is directed to these, as well as other, important ends.

SUMMARY OF THE INVENTION

The present invention relates to yeast-based expression systems for the production of desired polypeptides. The expression systems comprise a yeast host cell, selected from the group consisting of *Ogataea wickerhamii* (*O. wickerhamii*), *Ogataea kodamae* (*O. kodamae*), *Ogataea pini* (*O. pini*), *Komagataella pastoris* (*K. pastoris*), or *Zygosaccharomyces pastori* (*Z. pastori*) and a vector. The vector is adapted to express a nucleic acid molecule encoding a desired polypeptide, which nucleic acid molecule is operably linked to one or more regulatory regions. In some preferred embodiments the yeast host cell is *K. pastoris*.

The present invention also relates to methods for isolating a desired polypeptide from a yeast host cell. The methods comprise transforming a yeast cell with an expression vector comprising a nucleic acid molecule encoding a desired polypeptide, transforming the host cell with said expression vector, expanding the transformed host cells in culture, and isolating the desired polypeptide from the culture. In some preferred embodiments, the yeast host cell is *K. pastoris*. In some preferred embodiments, the vector comprises a *K. pastoris* alcohol oxidase gene promoter.

The present invention further relates to an isolated nucleic acid molecule having promoter activity having the nucleotide sequence of SEQ ID NO:1.

In related aspects, the present invention relates to polypeptide products produced by the novel expression systems described.

These and other aspects of our invention will become apparent from the disclosure and claims herein provided.

DETAILED DESCRIPTION OF THE INVENTION

Overview

Figure 1:
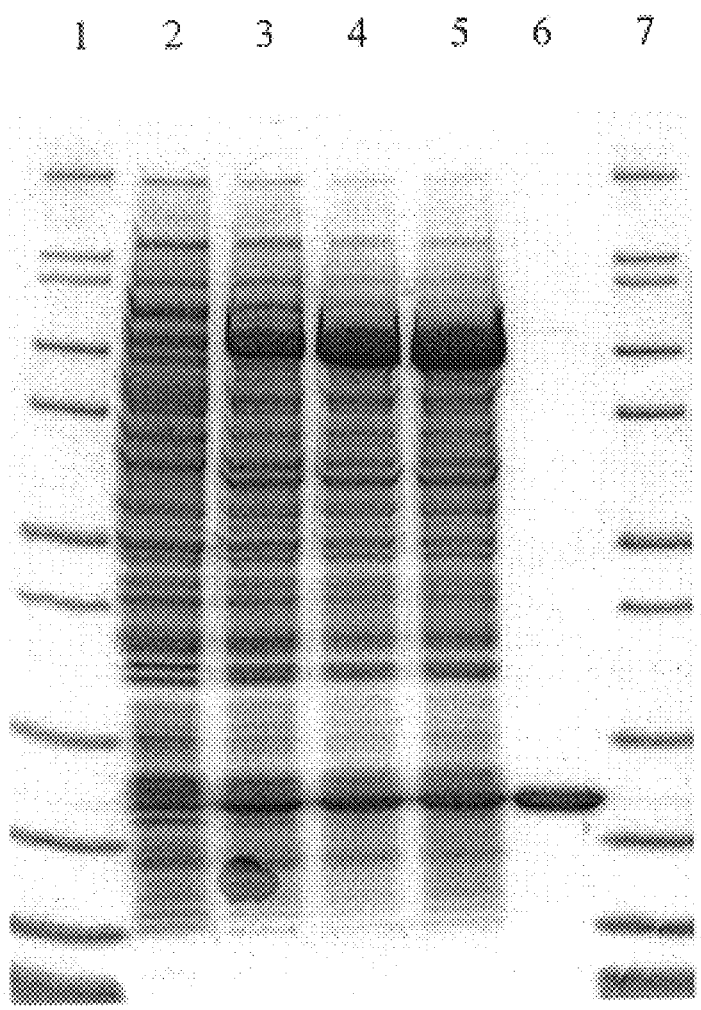
FIG. 1 depicts an SDS-polyacrylamide gel (SDS-PAGE) showing induction of TNF during fermentation of *K. pastoris*. Lanes 1 and 7, molecular weight standards (from top to bottom, in kilodaltons, 200, 116.3, 97.4, 66.3, 55.4, 36.5, 31, 21.5, 14.4, 6, 3.5); Lane 2, prior to induction with methanol; Lane 3, 1 day post-induction; Lane 4, 2 days post-induction; Lane 5, 3 days post-induction; Lane 6, purified TNF.
Figure 2:
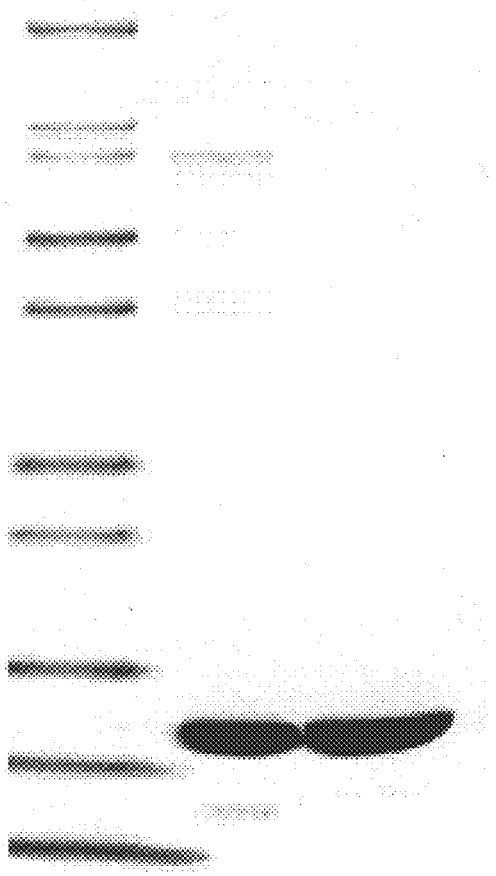
FIG. 2 depicts a SDS-polyacrylamide gel (SDS-PAGE) of TNF purified from *E. coli* and *K. pastoris*. Molecular weight standards (from top to bottom, in kilodaltons, 200, 116.3, 97.4, 66.3, 55.4, 36.5, 31, 21.5, 14.4, 6).
Figure 3:
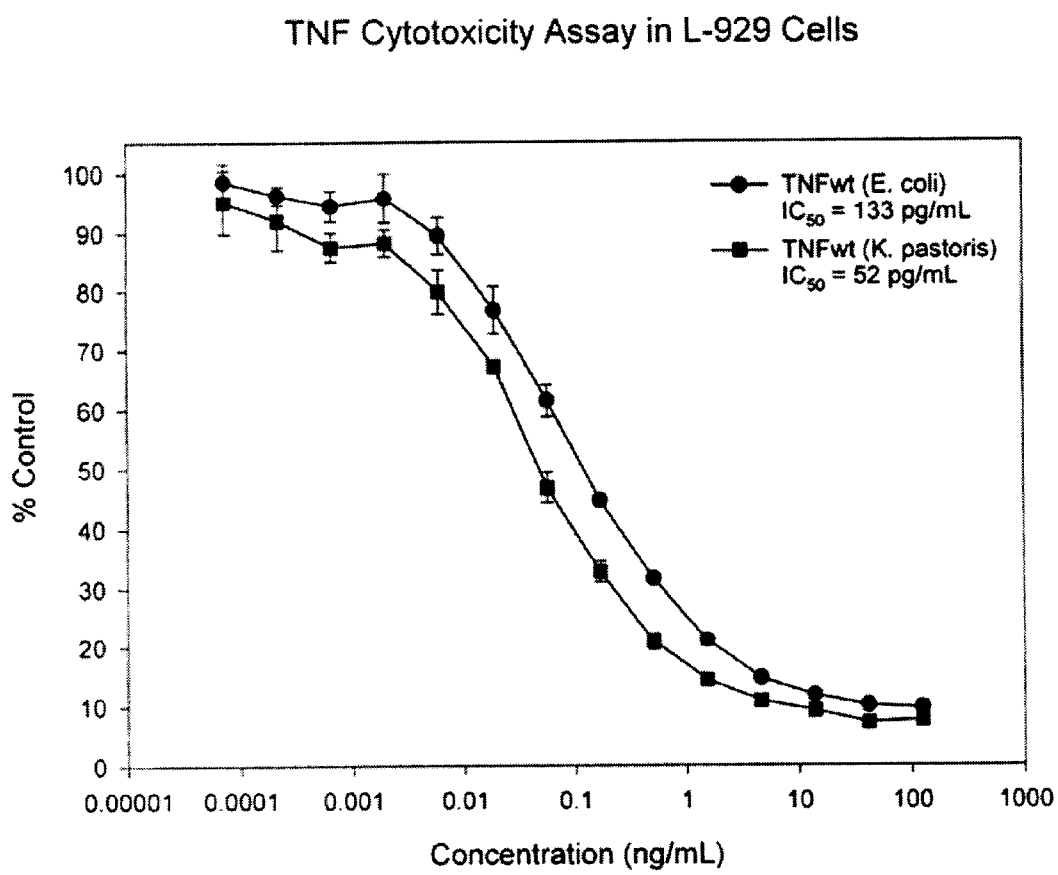
FIG. 3 depicts the results of an L929 Cytotoxicity assay-comparing TNF purified from *E. coli* and *K. pastoris*.

The present invention is based on the important discovery that certain strains of yeast may be used as hosts in expression systems for the production of polypeptides. The present invention is thus directed to expression systems that include certain yeast strains as host cells. The present invention is also directed to recombinant DNA molecules, recombinant vectors and regulatory regions for use in yeast-based expression systems. Such novel expression systems are useful, inter alia, for the production of desired polypeptides. In some embodiments, such polypeptides are used as industrial and pharmaceutical proteins and enzymes.

Transformed yeast cells can be used for the production of many different desired polypeptides including, but not limited to enzymes, growth factors, cytokines, immunogenic proteins, immunoglobulin proteins, such as single chain antibodies or antibody fragments, and so on. In a preferred embodiment, the yeast expression systems of the present invention produce a deiminase protein, more preferably arginine deiminase.

The present invention sets forth the unexpected finding that polypeptides can be produced in *K. pastoris* using the present invention where other expression systems fail. For example, arginine deiminase (ADI) can be produced in *K. pastoris* as a soluble, active enzyme. However, other expression systems fail to yield active ADI. In *E. coli*, for example, ADI is expressed in an inactive form as an inclusion body when expressed intracellularly. When ADI was expressed in *E. coil* as a periplasmic protein, the resulting protein lacked activity. When the yeast strain *P. pastoris* was used for expression of ADI, only a small amount of ADI was expressed, and the protein expressed lacked enzymatic activity.

Several elements are generally present in order for a host microorganism to be useful for the practice of recombinant DNA technology, including without limitation a host cell, and a vector comprising a nucleic acid molecule encoding a desired polypeptide.

Definitions

As used herein, the term expression system refers to components of a system for the production of a desired polypeptide. "Expression systems" of the present convention comprise, inter alia, a yeast host cell and a vector comprising a nucleic acid molecule encoding a desired polypeptide. The vector comprises regulatory regions operably linked to one or more nucleic acid sequences encoding one or more desired polypeptides. The vector is operably compatible with the yeast host cell.

As used herein the term "operably compatible" indicates that the vector of the expression system is able to function in the chosen host cell to produce the desired polypeptide.

As used herein, the term "methanol assimilating yeast" refers to those yeasts that can utilize methanol as a source of carbon and energy, and include, as non-limiting examples, yeasts of the genera Candida, Hansenula, Komagatella, Ogaatea, Pichia, Torulopsis, and Zygosaccharomyces.

As used herein, the term "transformation" refers to the uptake and incorporation of DNA in a host cell, wherein the introduced DNA may change the phenotype of the recipient cell.

As used herein, the term "heterologous nucleic acid sequence" refers to a nucleic acid sequence that does not exist naturally within a given host cell.

As used herein, the term "homologous nucleic acid sequence" refers to a nucleic acid sequence that exists naturally within a given host cell.

As used herein, the term "operably linked" indicates that nucleic acid sequences are arranged so that they function in concert for their intended purposes.

As used herein, the term "operably compatible" indicates that the vector of the expression system is able to function in the chosen yeast host to produce the desired polypeptide.

The term "regulatory region" is used herein for its art-recognized meaning to denote a nucleic acid sequence that directs the production of a polypeptide that is encoded by another nucleic acid sequence. Regulatory regions may include without limitation, a transcription promoter, a transcription terminator, activator sequences, and a yeast replication origin.

As used herein, the term "polypeptide" refers to any translation product of a nucleic acid molecule, regardless of size, whether or not glycosylated, phosphorylated or modified post-translationally. Examples of polypeptides contemplated by the instant invention include amino acids, proteins and peptides. "Desired polypeptides" refer to polypeptides encoded by a nucleic acid sequence gene, and that may be the result of a nucleic acid construct of the present invention, including polypeptides that are functionally equivalent or that are fragments of the polypeptides or selected polypeptides.

As used herein, the term "heterologous polypeptide" refers to a polypeptide that is not naturally expressed by a host cell of the present invention.

The term "promoter" is used herein for its art-recognized meaning to denote a nucleic acid sequence that provides for the binding of RNA polymerase and the initiation of transcription. A promoter may contain sequence elements that function in the initiation of transcription and may also be characterized by consensus nucleotide sequences. These sequence elements may include RNA polymerase binding sites, TATA sequences, CAAT sequences, differentiation-specific elements, cyclic AMP response elements, serum response elements, glucocorticoid response elements, and binding sites for other transcription factors such as CRE/ATF, SPI, cAMP response element binding protein and octamer factors. Promoters appropriate for use in the present invention include, but are not limited to, inducible promoters, constitutive promoters, and hybrid promoters.

Typically, a promoter is located in the 5' region of a gene and is proximal to the transcriptional start site of the gene. Promoters of the present invention are from about 100 to about 1000 nucleotides in length. In a preferred embodiment, the promoters are from about 200 to about 800 nucleotides in length.

As used herein, the term "inducible promoter" refers to a promoter that can be regulated. Preferred inducible promoters of the present invention are those that can be upregulated. Examples of yeast-derived inducible promoters include but are not limited to Ppmp20 and Ppmp47, methanol inducible promoters from *Candida boidinii*.

As used herein, the term "constitutive promoter" refers to a promoter which cannot be regulated; i.e., it is always "on" or "off".

As used herein, the term "hybrid promoter" refers to a promoter which comprises nucleic acid sequence from more than one source. For example, one exemplary hybrid promoter may contain part of a promoter from one source and part of a promoter from a second source.

As used herein, the term "terminator" or "transcription terminator" refers to a nucleic acid sequence at the end of the transcript that causes RNA polymerase to terminate transcription. Examples of terminators useful in the present invention include but are not limited to iso-1-cytohrome c gene transcriptional terminator and alcohol oxidase gene transcriptional terminator. In some preferred embodiments, the terminator is the *K. pastoris* AOX terminator.

As used herein, the term "yeast replication origin", also referred to a "origin of replication", refers to the site on a nucleic acid sequence at which replication is initiated. Yeast replication origins may be required in a recombinant vector capable of expressing a desired polypeptide in order for there to be replication of the vector, leading to significant expression of the desired polypeptide. Examples of yeast replication origins suitable for use in the present invention are described, for example, in U.S. Pat. No. 4,615,974 (Kingsman et al.), and include, but are not limited to, the 2$\mu$ plasmid replication system, or a functionally active portion thereof, and autonomous replicating sequences (ARS). Examples of ARS include but are not limited to ARS1 or ARS3.

As used herein, the term "host cell" refers to a microorganism that can be transformed with the vector carrying the nucleic acid molecule encoding a desired polypeptide wherein the host microorganism has the cellular apparatus to allow expression of the nucleic acid molecule encoding a desired polypeptide.

The term "percentage of sequence identity" or "percentage of sequence homology" is calculated by comparing two optimally aligned sequences over that region of comparison, determining the number of positions at which the identical nucleic acid base (e.g., A, T, C, G, U, or I, in the case of nucleic acids) occurs in both sequences to yield the number of matched positions, dividing the number of matched positions by the total number of positions in the region of comparison (i.e., the window size), and multiplying the result by 100 to yield the percentage of sequence identity. The term "substantial identity" as used herein denotes a characteristic of a polynucleotide sequence, wherein the polynucleotide comprises a sequence that has at least 80 percent sequence identity, preferably at least 85 percent identity and often 90 to 95 percent sequence identity, more usually at least 99 percent sequence identity as compared to a reference sequence over a comparison region.

A determination of homology or identity is typically made by a computer homology program known in the art. An exemplary program is the Gap program (Wisconsin Sequence Analysis Package, Version 8 for UNIX, Genetics Computer Group, University Research Park, Madison, Wis.) using the default settings, which uses the algorithm of Smith and Waterman (Adv. Appl. Math., 1981, 2: 482–489, which in incorporated herein by reference in its entirety). Employing the GAP software provided in the GCG program package, (see Needleman and Wunsch 1970 *J. Mol Biol* 48: 443–453) the following settings for nucleic acid sequence comparison may be used: GAP creation penalty of 5.0 and GAP extension penalty of 0.3, the coding region of the analogous nucleic acid sequences referred to above exhibits a degree of identity preferably of at least 70%, 75%, 80%, 85%, 90%, 95%, 98%, or 99%, with the sequence shown in SEQ ID NO:1.

Alternatively, homology may be determined by hybridization analysis wherein a nucleic acid sequence is hybridized to the complement of a sequence encoding the aforementioned proteins under stringent (i.e., high stringency), moderately stringent, or low stringent conditions.

As used herein "high stringency hybridization conditions" means hybridization at 42EC in the presence of 50% formamide; a first wash at 65° C. with 2× SSC containing 1% SDS; followed by a second wash at 65° C. with 0.1× SSC.

As used herein, "moderate stringency hybridization conditions" means hybridization at 55° C. with 6× SSC containing 0.5% SDS; followed by two washes at 37° C. with 1× SSC.

As used herein, the term "vector" refers to a nucleic acid molecule into which nucleic acid fragments DNA may be inserted or cloned. The vector serves to transfer the nucleic acid molecule encoding a desired polypeptide into a host microorganism, maintain the nucleic acid molecule in the host microorganism as well as provide a high level of expression of the nucleic acid sequence.

Yeast Host Cells

In certain embodiments, the yeast host cell is a strain of methanol assimilating yeast. In some preferred embodiments, the yeast host cell is selected from the group consisting of *Ogataea wickerhamii* (*O. wickerhamii*), *Ogataea kodamae* (*O. kodamae*), *Ogataea pini* (*O. pini*), *K. pastoris*, or *Zygosaccharomyces pastori* (*Z. pastori*). In a more preferred embodiment, the yeast host cell is *K. pastori*.

It has been found that *O. wickerhamii*, *O. kodamae*, *O. pini*, *K. pastoris*, and *Z. pastori* are highly efficient host cells for the production of desired polypeptides. Additionally, such host cells yield polypeptides that are glycosylated and substantially free of toxic pyrogenic factors. Further, such host cells may be utilized to produce desired polypeptides as secreted polypeptides, facilitating purification.

The expression systems of the present invention include yeast cells as hosts for the production of desired polypeptides. *O. wickerhamii, O. kodamae, O. pini, K. pastoris*, and *Z. pastori* have not been used before for the production of desired polypeptides in part because suitable promoters for the expression of desired polypeptides have not been identified in these organisms. Further, it is unpredictable whether such strains of yeast would function for the production of polypeptides, and, if they are in fact useful for the production of polypeptides, what conditions would most efficiently yield the desired polypeptide, and whether polypeptide products would be appropriately glycosylated and/or free of toxic pyrogenic factors.

These yeast can grow rapidly on simple defined medium to high cell densities. Yeast can be grown in medium containing appropriate sources of carbon, nitrogen and other elements, as well as trace nutrients. YPD growth medium is preferred (2% glucose, 2% peptone, 1% yeast extract). For recombinant protein production, growth of minimal medium containing methanol (6.7 g/L yeast nitrogen base without amino acids, 0.5% methanol, 0.4 µg/L biotin) is preferred.

In addition, the promoters of certain genes in these yeast are tightly regulated and very strong, making them capable of producing large amounts of recombinant protein under induced or de-repressed conditions. This makes these yeast especially useful for the production of proteins and peptides of commercial value without the need for extensive post-translational processing as is required, for example, using *E. coli* as a host cell. See, for example, Faber et al., Yeast 11:1331 (1995), and Cregg et al., Bio/Technology 11:905 (1993), the disclosures of which are hereby incorporated by reference herein in their entirety.

Temperatures from about 22° C. to about 35° C. may be used for growth of yeast with the preferred temperature of about 30° C. Yeasts can be cultured on liquid medium or on solid medium containing agar. For growth in liquid cultures, adequate aeration must be provided by rapid shaking of flasks or by sparging of fermentors.

Culturing of yeast cells is known to those skilled in the art. *K. pastoris* cells, for example, can be cultured in a medium containing adequate sources of carbon, nitrogen and trace nutrients at a temperature of about 25° C. to 32° C. Liquid cultures are provided with aeration by shaking of small flasks or tubes or sparging of fermentors. Suitable culture mediums are well known to those skilled in the art. A preferred culture medium is YPD (2% peptone, 1% yeast extract, 2% D-glucose; Difco, Detroit, Mich.). The cells may be passaged by dilution into fresh culture medium or stored for several days to weeks on plates in a refrigerator. For long-term storage, the cells are kept in a 50% glycerol solution at −70° C.

Vectors

The present invention further provides vectors for use in yeast-based expression systems. The vector comprising a nucleic acid sequence encoding the desired polypeptide can be introduced into the yeast host cell via, for example, transformation. By growing the transformed yeast under appropriate conditions, large quantities of the vector can be obtained.

In some preferred embodiments, the expression systems of the present invention comprise vectors comprising operably linked elements including a nucleic acid molecule encoding a heterologous and/or homologous polypeptide, a transcription promoter, and a transcription terminator.

Preferred vectors preferably contain a promoter that is recognized by the yeast host and include, but are not limited to, plasmids, phages, cosmids, episomes, viral particles or viruses, and integratable nucleic fragments (i.e., fragments integratable into the host genome by homologous recombination). Preferred viral particles include, but are not limited to, adenoviruses, baculoviruses, parvoviruses, herpesviruses, poxviruses, adeno-associated viruses, Semliki Forest viruses, vaccinia viruses, and retroviruses. Preferred expression vectors include, but are not limited to, pAO815, pGAPZ, pGAPZα, pPIC3.5K, pPIC6, pPIC6α, pPIC9, pPICZ, pPICZα, pPICZ-E, pPICZα-E, pMET, and pMETα, each available from Invitrogen (Carlsbad, Calif.). Expression vectors are preferably utilized for production of one or more desired polypeptides, but may also be utilized simply to amplify a nucleic acid sequence that encodes a desired polypeptide. In preferred embodiments, the vector is an expression vector wherein the nucleic acid molecule encoding a desired polypeptide is operably linked to one or more regulatory regions. Autonomously replicating recombinant expression constructs such as plasmid and viral DNA vectors incorporating nucleic acid molecules encoding a desired polypeptide are also provided.

Vectors can include an appropriate marker that allows the screening of the transformed host cells. The transformation of the selected host is carried out using any one of the various techniques well known to the expert in the art and described in Sambrook et al., supra.

Amplification vectors do not require expression control domains, but rather need only the ability to replicate in a host, usually conferred by an origin of replication, and a selection gene to facilitate recognition of transformants. The need for regulatory regions in the expression vector will vary depending upon the host selected and the transformation method chosen.

Additional regulatory regions can also be included in preferred vectors. Preferred examples of suitable additional regulatory region sequences are represented by the Shine-Dalgarno of the replicase gene of the phage MS-2 and of the gene cII of bacteriophage lambda.

In a preferred embodiment, the vector is a plasmid. In addition to those plasmids that have been found to occur naturally in microorganisms, a variety of man-made plasmids, or hybrid vectors, are available. For example, a plasmid can be specifically cleaved by one or another restriction endonuclease or restriction enzyme, each of which recognizes a specific, unique site on the plasmid. Thereafter, homologous nucleic acid molecules, heterologous nucleic acid or fragments of nucleic acid molecules may be inserted into the plasmid by endwise joining of the cleaved plasmid and desired genetic material at the cleavage site or at reconstructed ends adjacent to the cleavage site. The resulting recombined material can be referred to as a hybrid vector. In addition, naturally occurring and hybrid vectors generally contain nucleic acids that encodes a variety of information including that information required to reproduce the plasmid in daughter cells, i.e., an autonomously replicating sequence or an origin of replication. Such vectors also generally encode one or more phenotypic selection characteristics. Phenotypic selection characteristics may permit clones of the host cell containing the plasmid of interest to be recognized and selected by preferential growth of the cells in selective media.

When the nucleic acid sequence is inserted in the correct orientation with reference to the portions of the vector which govern transcription and translation of the encoded nucleic acid sequence, the resulting vector can be used to direct the production of the desired polypeptide.

In some embodiments, the expression system of the present invention includes vectors and promoters suitable for use with yeast. In certain embodiments, the vectors and promoters are suitable for use with methanol-assimilating yeast. Many genes from methanol-assimilating yeasts are well known by those skilled in the art and may include, without limitation, genes encoding alcohol oxidase, dihydroxyacetone synthase, formate dehydrogenase, and catalase genes. Components such as promoters, coding sequences and transcriptional terminators from such genes may be used in expression vectors. Many other vectors suitable for use in the present invention are well known in the art and may include, by way of example only, *E. coli* vectors such as pUC18, pUC19 and pBR322. Additional vectors include, without limitation, methanophil bacterium and *S. cerevisiae* promoters.

In certain embodiments, the heterologous nucleic acid molecule encoding the desired polypeptide may further comprise a nucleic acid molecule encoding a selectable marker. This selectable marker may allow the transformed cells to grow under conditions in which non-transformed cells cannot multiply ("selective conditions"). The general principles of selection are well known by those skilled in the art. Commonly used selectable markers are DNA sequences that encode enzymes required for the synthesis of amino acids or nucleotides. Cells having mutations in these genes cannot grow in media lacking the specific amino acid or nucleotide unless the mutation is complemented by the selectable marker. Use of such "selective" culture media ensures the stable maintenance of the heterologous nucleic acid within the host cell. In another embodiment of the invention, a dominant selectable marker may be used. Dominant selectable markers are those markers that provide a growth advantage to transformed cells. Dominant selectable markers include but are not limited to DNA sequences that provide resistance to antibiotics, such as neomycin-type antibiotics (e.g., G418), hygromycin B and bleomycin/phleomycin-type antibiotics such as Zeocin™ (Invitrogen Corporation, San Diego, Calif.). In addition, the expression systems of the present invention may comprise a vector comprising a nucleic acid molecule fragment of an autonomously replicating sequence of a methanol assimilating yeast which is inserted into the vector in place of or in addition to the marker gene.

In some preferred embodiments, the selectable marker is the neomycin phosphotransferase gene from transposon Tn5, which confers resistance against neomycin type antibiotics, preferably G418.

Promoters

Promoters useful in the present invention may be of eukaryotic, prokaryotic, or viral origin. As described above, promoters may also be of an artificial origin, e.g. hybrid promoters. Examples of promoters appropriate for use in the present invention include, but are not limited to alcohol oxidase gene promoter, dihydroxyacetone synthase gene promoter, formate dehydrogenase gene promoter, elongation factor 1-alpha gene promoter, and catalase gene promoter, simian virus 40 promoter, mouse mammary tumor virus promoter, long terminal repeat of human immunodeficiency virus promoter, maloney virus promoter, cytomegalovirus immediate early promoter, Epstein Barr virus promoter, rous sarcoma virus promoter, human actin promoter, human myosin promoter, human hemoglobin promoter, human muscle creatine promoter, and human metalothionein promoter.

A preferred promoter is a methanol-inducible promoter, preferably that of a *K. pastoris* alcohol oxidase gene. The sequence of the *K. pastoris* AOX promoter is shown in SEQ ID NO: 1. Other promoters suitable for use in the present invention include those of the dihydroxyacetone synthase (DHAS), formate dehydrogenase (FMD), and catalase (CAT) genes. Genes encoding these enzymes from other species have been described, and their sequences are available (e.g., Janowicz et al., Nuc. Acids Res., 13:2043, 1985; Hollenberg and Janowicz, EPO publication 0299 108; Didion and Roggenkamp, FEBS Lett. 303:113, 1992). Genes encoding these proteins can be cloned by using the known sequences as probes for screening K pastoris genomic libraries, or by aligning the known sequences, designing primers based on conserved sequences found in the alignment, and amplifying K pastoris DNA using, for example, the polymerase chain reaction (PCR).

The invention also includes homologs of the *K. pastoris* AOX promoter, in general, preferably at least 60%, at least 65%, at least 70%, at least 75%, at least 80%, at least 85%, at least 90%, at least 95%, at least 98%, or at least 99% identity with the AOX promoter of the invention. Generally, percent sequence "identity" (or "homology") with respect to polynucleotides of the invention may be calculated as the percentage of nucleotide bases in the candidate sequence that are identical to nucleotides in the *K. pastoris* AOX promoter sequence set forth in SEQ ID NO: 1, after aligning the sequences and introducing gaps, if necessary, to achieve the maximum percent sequence identity.

In a preferred embodiment, the vectors of the present invention comprise a plasmid comprising a promoter from an alcohol oxidase (AOX) gene of *K. pastoris* operably linked to the AOX transcriptional terminator. Between the AOX promoter and the transcriptional terminator is a multiple cloning site for the insertion of one or more heterologous nucleic acid sequences for expression under the control of the AOX promoter. In addition, the plasmid may further comprise a nucleic acid molecule encoding the neomycin phosphotransferase gene from transposon Tn5, which confers resistance against neomycin type antibiotics, preferably G418. This allows for the direct selection of transformed yeast by G418 resistance. Expression of the neomycin phosphotransferase gene is controlled by the elongation factor 1-alpha gene promoter from *S. cerevisiae* and allows for consititutive expression of neomycin phophotransferase in transformed yeast. The iso-1-cytochrome c gene transcriptional terminator, also from *S. cerevisae*, is linked to the 3'-end of the neomycin phosphotransferase coding sequence, and ensures proper transcriptional termination of the neomycin phophotransferase messenger RNA. The backbone of the plasmid is derived from pUC-19 and contains an *E. coli* origin of replication and beta-lactamase gene for replication and selection of the plasmid in *E. coli*.

Kits

In some embodiments of the present invention, kits are provided comprising a yeast host cell selected from the group consisting of *Ogataea wickerhamii, Ogataea kodamae, Ogataea pini, Komagataella pastoris*, and *Zygosaccharomyces pastori*, and a vector. In some preferred embodiments, the vector is an expression vector comprising a nucleic acid encoding a desired polypeptide. In other embodiments, the vector comprises one or more cloning sites for insertion of one or more nucleic acids encoding a desired polypeptide operably linked to one or more regulatory regions. Optionally, kits may also contain one or more of the following: instructions for use, media for growth of yeast host cells, materials for growth under selective conditions, materials for transformation of yeast cells, photographs of representative examples of positive results and photographs of representative examples of negative results, and molecular weight standards for sizing of an expressed polypeptide product.

Transformation and Culture of Yeast Cells

The expression systems of the present invention may be obtained via recombinant DNA technology, in particular through the transformation of a yeast with a nucleic acid sequence coding a desired polypeptide together with one or more other nucleic acid sequences which regulate the expression of the coding sequence in a particular yeast or group of yeast. The basic techniques employed in the field of recombinant DNA technology are well known by those skilled in the art. See, for example, Sambrook et al., "Molecular Cloning: A Laboratory Manual" 3rd Edition, Cold Spring Harbor Laboratory Press, Cold Spring Harbor, N.Y. (2001).

Those skilled in the art are familiar with a variety of transformation techniques, including introduction of an episomal vector containing a nucleic acid sequence or a vector containing nucleic acid sequences which is also equipped with nucleic acid sequences capable of being integrated into the chromosome of the microorganism. See, for example, Maniatis et al, and Sambrook et al.

In practice, the use of recombinant DNA technology can create microorganisms capable of expressing entirely heterologous polypeptides, i.e., polypeptides not ordinarily found in, or produced by, a given microorganism—so called "direct expression". Alternatively, there may be expressed a fusion protein, i.e., a heterologous polypeptide fused to a portion of the amino acid sequence of a homologous polypeptide, i.e., polypeptides found in, or produced by, the wild-type (non-transformed) host microorganism—so called "indirect expression". With indirect expression, the initially obtained fusion polypeptide product is sometimes rendered inactive for its intended use until the fused homologous/heterologous polypeptide is cleaved in a particular environment (often extracellularly).

Yeast cells can be transformed with many types of nucleic acid molecules, including but not limited to DNA, RNA or mRNA. Yeast cells may also be transformed with nucleic acid libraries and synthetic nucleic acid molecules. The present invention thus provides inter alia, for the expression of genetically diverse libraries for the production of products that can be screened for novel biological activities, to engineer cells for use as targets for the screening of compound libraries, and to genetically modify cells to enhance their utility within other processes.

It is preferred that the nucleic acid sequence encoding a polypeptide can be regulated, i.e., switched "on" or "off", because this allows for biomass production, when desired, by selecting a suitable substrate. For example, regulation may allow for production of the polypeptide, when desired, by using methanol or mixtures of methanol and/or other carbon sources. Because methanol is an inexpensive substrate, polypeptide production may be extremely economical. Accordingly, the expression systems of the present invention may further comprise a nucleic acid molecule comprising a transcription promoter of a particular gene, wherein the nucleic acid molecule is essentially free of coding sequence of the gene.

Heterologous nucleic acids can be introduced into host yeast gene cells by any of a number of known methods. These methods include, but are not limited to, spheroplast transformation (Beggs, Nature 275:104, 1975; Cregg et al., Mol. Cell. Biol. 5:3376, 1985), lithium transformation (Hiep et al., Yeast 9:1189–1197, 1993; Bogdanova et al., Yeast 11:343, 1995), polyethylene glycol transformation (Kleve et al., Gene 25:333–341, 1983; Dohmen et al., Yeast 7:691–692, 1991), or electroporation. In some preferred embodiments of the present invention, polyethylene glycol transformation (Dohmen et al., Yeast 7:691–692, 1991) is used to introduce DNA into yeast host cells. DNA molecules used for the transformation of yeast host cells are usually prepared as double-stranded, circular plasmids that are linearized prior to transformation. Although details of transformation of $K.$ $pastoris$ are given in the examples below, other yeast host cells may be transformed using similar techniques.

In one embodiment using direct selection of G418 resistance in $K.$ $pastoris$, YPD broth may be added to the transformation mixture and the mixture incubated at 30° C. with shaking at 200–250 rpm for a period of time. Aliquots of the transformation are then plated directly on YPD agar medium containing G418. The plates are then incubated at about 25° C. to about 32° C. for from about 1 to about 6 days, or until colonies appear. In a preferred embodiment, plates are incubated at about 30° C. for about 6 days.

In many cases integration of multiple copies of recombinant genes in yeasts can increase the expression of the desired polypeptide (Cregg et al., Bio/Technology 11:905–910 (1993), Romanos et al., Curr. Opin. Biotech. 6:527–533 (1995), Scorer et al., Bio/Technology 12;181–184 (1994)). Screening for resistance to high levels of G418 can identify transformed yeast containing multicopy inserts. The level of resistance to G418 corresponds roughly to the number of neomycin resistance genes integrated into the yeast chromosome. Transformants resistant to high levels of G418 should contain multiple copies of the expression cassette, and thus may exhibit increased expression of the desired protein.

G418 resistant transformants can be directly screened for the production of the recombinant protein. Yeast host cells transformed with an expression vector carrying a methanol inducible promoter linked to the nucleic acid encoding the desired polypeptide may be grown in the presence of methanol as the sole carbon source. Transformed yeast cells can be grown in shake flasks containing minimal medium with methanol (6.7 g yeast nitrogen base without amino acids (Difco), 5 g/L methanol, 0.4 $\mu$g/L biotin) at 30° C. with vigorous shaking for 2 to 4 days.

For large-scale production, yeast host cells can be grown to high cell densities in a fermentor. An inoculum is produced by growing the cells using YPD in a shake flask incubated at 30° C. with vigorous agitation for 1 to 2 days. The inoculum is then used to seed a fermentor containing a suitable medium containing salts, glycerol, trace elements and biotin at 30° C., pH 5.0, and >30% dissolved oxygen. The cells are allowed to grow in the fermentor until all of the glycerol is consumed. A glycerol feed is then initiated to further increase the biomass of the culture. After the glycerol feed is completed, a methanol feed is started to induce expression of the recombinant protein. The methanol feed is typically continued for 1 to 4 days. A cell density of from about 200 to 400 grams of wet cell paste per liter is obtained.

Recovery of Polypeptides

Polypeptides may be recovered by means well known to those of skill in the art. See The expression systems of the present invention may also provide nucleic acid sequences which direct the incorporation of the desired polypeptide into peroxisomes. Peroxisomes are intracellular bodies present in large amounts in methanol grown yeast cells. These intracellular bodies may serve to isolate the incorporated polypeptide product from intracellular fluids and enzymes such as proteases.

The expression systems of the present invention may also provide for secretion of the desired polypeptide. Secretion of the desired polypeptide may be desirable for a number of reasons. Secretion into the medium can make purification of the polypeptide easier because it is not necessary to break open the host cells and purify the polypeptide away from the host cell protein. Since relatively few host cell proteins are secreted, this makes removal of contaminating host cell proteins away from the desired polypeptide simpler and more cost effective. In some cases, where a recombinant polypeptide may be toxic to the host cell, secretion into the medium may prevent the buildup of the polypeptide to toxic levels inside the cell. Additionally, some polypeptides are not produced in an active form until they are secreted.

For the secretion of polypeptides by a host cell, a signal peptide attached to the N-terminus of the mature secreted polypeptide may be required. The signal peptide is recognized by the transport mechanisms of the host cell and marks a protein for secretion through the host cell membrane. The signal peptide is typically cleaved off during the transport process with the mature protein being released into the medium. Secretion of recombinant proteins can be accomplished by linking the coding sequence of the recombinant protein with the nucleotide sequence of a signal peptide.

EXAMPLES

The invention is further demonstrated in the following examples, which are for purposes of illustration, and are not intended to limit the scope of the invention.

Example 1

Isolation of AOX Gene Segments from K. pastoris

The AOX promoter, part of the AOX coding sequence, and the AOX transcriptional terminator were isolated from K. pastoris using PCR. PCR primers were based on the published sequences of the AOX1 promoter, coding sequence and AOX1 transcriptional terminator from Pichia pastoris (GenBank Accession No. E00913, GenBank Accession No. U96967). For isolation of the AOX promoter, the primers had the following sequences:

```
                                    (SEQ. ID. NO.2)
MOfor1: 5'-GGAGCTCGCTCATTCCAATTCC-3'

(SEQ. ID. NO.3)
AOrev:  5'-GTGTGGTCACCGAAGAA-3'
```

For isolation of the AOX transcriptional terminator:

```
                                    (SEQ. ID. NO.4)
AOTTfor: 5'-GTGAAGCTTCAAGAGGATGTCAGAATGCC-3'

(SEQ. ID. NO.5)
AOTTrev: 5'-CACACATGTGTGGGAAATACCTTGAAAAACATC-3'
```

The PCR for isolating the AOX promoter and 5' coding sequence was carried out using genomic DNA isolated from K. pastoris (ATCC 28485) and the MOfor (SEQ. ID. NO. 2) and AOrev (SEQ. ID. NO. 3) primers. The reaction contained 1× ExTaq PCR buffer (TaKaRa), 100 ng of purified genomic DNA from K pastoris, 0.2 mM dNTPs, 1 μM of each primer, and 1.25 U of ExTaq polymerase (TaKaRa). The PCR conditions were as follows: 94° C. for 2 minutes, followed by 35 cycles of 94° C. for 30 seconds, 50° C. for 30 seconds, and 72° C. for 1 minute. The 35 cycles were followed by incubation at 72° C. for 10 minutes. The PCR produced a product of 1,958 bp. The PCR product was subcloned into pCR2.1, creating pCR2.1:AOX-1 (Invitrogen), and the AOX product was sequenced. Sequencing of the product (SEQ. ID. NO. 6) and subsequent alignment revealed about 90% homology with the AOX1 promoter from Pichia pastoris (GenBank Accession No. E00913).

The alcohol oxidase gene transcriptional terminator was isolated from K. pastoris using PCR using genomic DNA isolated from K. pastoris (ATCC 28485) and the AOTTfor (SEQ. ID. NO. 4) and AOTTrev (SEQ. ID. NO. 5) primers. The reaction contained 1× ExTaq PCR buffer (TaKaRa), 100 ng of purified genomic DNA from K. pastoris, 0.2 mM dNTPs, 1 μM of each primer, and 1.25 U of ExTaq polymerase (TaKaRa). The PCR conditions were as follows: 94° C. for 2 minutes, followed by 94° C. for 30 seconds, 50° C. for 30 seconds, and 72° C. for 1 minute for 30 cycles. The 30 cycles were followed by incubation at 72° C. for 10 minutes. The PCR produced a product of 234 bp. The PCR product was subcloned into pCR2.1 (Invitrogen) for sequencing. Sequencing of the PCR product corresponding to that of the transcriptional terminator (SEQ. ID NO. 7) revealed about 100% homology with the AOX1 transcriptional terminator from P. pastoris (GenBank Accession No. U96967).

Example 2

Construction of the G418 Resistance Cassette

A G418 resistance cassette was constructed and used for selection of transformed yeast using G418 resistance. The cassette consists of the neomycin phosphotransferase gene, the elongation factor 1-alpha gene promoter and iso-1-cytochrome c gene transcriptional terminator. PCR was used to isolate the neomycin phosphotransferase gene from the Tn5 transposon. The elongation factor 1-alpha (tef-1) gene promoter and iso-1-cytochrome c (cyc-1) gene transcriptional terminator were isolated from Saccharomyces cerevisiae using PCR. The sequences of the primers used in the PCR are as follows:

For isolation of the neomycin phosphotransferase coding sequence:

```
                                    (SEQ. ID. NO.8)
KANfor: 5'-GTGACTAGTATGATTGAACAAGATGG-3'

(SEQ. ID. NO.9)
KANrev: 5'-CACGCGGCCGCTCAGAAGAACTCGTCAAG-3'
```

For isolation of the tef-1 promoter:

```
                                    (SEQ. ID. NO.10)
TEFfor: 5'-GTGAATATTCCCACACACCATAGCTTC-3'

(SEQ. ID. NO.11)
TEFrev: 5'-CACACTAGTAAACTTAGATTAGATTGC-3'
```

For isolation of the cyc-1 transcriptional terminator:

```
                                     (SEQ. ID. NO.12)
CYCTTfor: 5'-GTGGCGGCCGCGGCCCCTTTTCCTTTGTCG-3'

(SEQ. ID. NO.13)
CYCTTrev: 5'-CTCAATATTAAGCTTGCAAATTAAAGCCTTCGAGC-3'
```

PCR for isolating the neomycin phosphotransferase coding sequence was carried out using a cell suspension of Escherichia coli containing the Tn5 neomycin phosphotransferase gene as a template and KANfor (SEQ. ID. NO. 8) and KANrev (SEQ. ID. NO. 9) primers. These primers place a Spe I restriction endonuclease site at the 5' end and a Not I site at the 3' end of the neomycin phosphotransferase coding sequence. PCR for isolating the tef-1 promoter was performed using genomic DNA isolated from *S. cerevisae* as a template and the TEFfor (SEQ. ID. NO. 10) and TEFrev (SEQ. ID. NO. 11) primers. These primers place SspI and SpeI restriction endonuclease sites at the 5' and 3' ends, respectively, of the tef-1 promoter sequence. PCR for isolating the cyc-1 transcriptional terminator was performed using genomic DNA isolated from *S. cerevisae* as a template and the CYCTTfor (SEQ. ID. NO. 12) and CYCTTrev (SEQ. ID. NO. 13) primers. The use of these primers places SspI and SpeI restriction endonuclease sites at the 5' and 3' ends, respectively, of the cyc-1 transcriptional terminator sequence. The PCRs for isolating the three components of the G418 resistance cassette contained 1× ExTaq PCR buffer (TaKaRa), 100 ng of purified genomic DNA from *S. cerevisiae*, 0.2 mM dNTPs, 1 μM of each primer, and 1.25 U of ExTaq polymerase (TaKaRa). The PCR conditions were as follows: 94° C. for 2 minutes, followed 94° C. for 30 seconds, 50° C. for 30 seconds, and 72° C. for 1 minute for 30 cycles. The 30 cycles were followed by incubation at 72° C. for 10 minutes. The PCR produced a neomycin phosphotransferase coding sequence product of 815 bp, a tef-1 promoter product of 428 bp and a cyc-1 transcriptional terminator product of 296 bp. All three PCR products were subcloned into pCR2.1 (Invitrogen) for sequencing.

For construction of the G418 resistance cassette, the tef-1 promoter and cyc-1 transcriptional terminator were excised from the respective pCR2.1 vectors and ligated into a pCR2.1 vector containing the neomycin phosphotransferase coding sequence as follows. It was first necessary to select a pCR2.1 vector which had the neomycin phosphotransferase coding sequence inserted in the correct orientation to ensure the proper location of restriction sites for subcloning. Several transformants from the pCR2.1 subcloning of the neomycin phosphotransferase coding sequence were grown and the plasmids isolated from each. The orientation of the neomycin phosphotransferase coding sequence was determined by digestion of the plasmids with NotI. A pCR2.1 containing the neomycin phosphotransferase coding sequence in the desired orientation will release a 33 bp fragment upon digestion with NotI. One such plasmid, pCR2.1:KAN, was selected and digested with BamHI and SpeI. pCR2.1:TEF was also digested with BamHI and SpeI and the 409 bp fragment containing the tef-1 promoter was ligated into pCR2.1:KAN to produce pCR2.1:TEF-KAN. It was also necessary to select a pCR2.1 subclone containing the cyc-1 transcriptional terminator in a particular orientation to ensure the proper location of restriction endonuclease sites used for subcloning. The orientation of the cyc-1 transcriptional terminator was determined by digestion with NotI and EcoRV. One plasmid, pCR2.1:CYC, with the cyc-1 transcriptional terminator in the desired orientation was digested with NotI and EcoRV and the approximately 300 bp fragment was ligated into the NotI-EcoRV sites of pCR2.1:TEF-KAN. The resulting plasmid, p-CR2.1:TEF-KAN-CYC, contains the neomycin phosphotransferase coding sequence under the control of the tef-1 promoter, with the cyc-1 transcriptional terminator at the 3' end of the coding sequence.

Example 3

The yeast expression vector was constructed as follows. pUC19 was digested with SacI, treated with Klenow fragment to remove the 3' overhangs of the digested plasmid, and then re-ligated. This removes the SacI site from the multiple cloning site of pUC19. The AOX transcriptional terminator was excised from pCR2.1:AOXTT by digesting with HindIII and AflII and ligated into pUC19 that had been digested with the same two restriction endonucleases. The resulting plasmid is designated pPX-1.

PCR was used to place Nde I and Eco RI restriction endonuclease sites at the 5' and 3' ends, respectively of the AOX promoter from *K. pastoris*. For this PCR, the forward and reverse primers had the following sequences:

```
                                      (SEQ. ID. NO. 14)
MOfor2: 5'GTGCATATGTGGAGCTCGCTCATTCCAAT-3'

(SEQ. ID. NO. 15)
MOrev:  5'CACGAATTCTTCGAATAATTAGTTGTTTTTG-3'
```

The PCR contained 1X ExTaq PCR buffer (manufacturer), 10 ng of purified pCR2.1:AOX-1 as template, 0.2 mM dNTPs, 1 μM of each primer, and 1.25 U of ExTaq polymerase (TaKaRa). PCR conditions were as follows: 94° C. for 2 minutes, followed by 30 cycles of 94° C. for 30 seconds, 50° C. for 30 seconds, and 72° C. for 1 minute. The 30 cycles were followed by incubation at 72° C. for 10 minutes. The PCR produced a product of 755 bp. The PCR product was subcloned into pCR2.1 (Invitrogen) creating pCR2.1:PAOX.

The AOX promoter from pCR2.1:PAOX was excised with NdeI and EcoRI and ligated into the NdeI-EcoRI sites of pPX-1. The resulting plasmid, pPX-2, contains the AOX promoter linked to the multiple cloning site of pUC-19 followed by the AOXTT. A gene inserted into the multiple cloning site will be expressed under the control of the AOX promoter. The presence of the AOX transcriptional terminator ensures that the 3' end of the transcript will be terminated correctly. For insertion of the G418 resistance cassette, pPX-2 was digested with NdeI treated with Klenow polymerase to create blunt ended DNA and then treated with alkaline phosphatase. The G418 resistance cassette was excised from p-CR2.1:TEF-KAN-CYC with SstI and ligated into pPX-2. Two possible orientations of the G418 resistance cassette are possible. Two plasmids, designated pPENX-1 (SEQ. ID. NO. 16) and pPENX-2 (SEQ. ID. NO. 17), resulted from this ligation. The only difference between pPENX-1 and pPENX-2 is the G418 resistance cassette is in opposite orientations in these plasmids. The presence of the G418 resistance expression cassette allows for the selection of yeast transformed with pPENX-1 or pPENX-2.

Example 4

Ligation of the Coding Sequence for Mature Human Tumor Necrosis Factor (TNF) into pPENX-1 and pPENX-2

PCR was used to place an EcoRI site at the 5' end and a BamHI site at the 3' end of the mature human TNF coding sequence. The sequences of the primers used for the PCR are shown below.

```
                                       (SEQ. ID. NO.18)
TNFforE: 5'-CTCGAATTCACCATGGTCAGATCATCTTC-3'

(SEQ. ID. NO.19)
TNFrevB: 5'-GAGGGATCCTCACAGGGCAATGATCC-3'
```

The PCR contained 1× ExTaq PCR buffer (TaKaRa), 10 ng of purified pCR2.1:AOX-1 as template, 0.2 mM dNTPs, 1 μM of each primer, and 1.25 U of ExTaq polymerase (TaKaRa). PCR conditions were as follows: 94° C. for 2 minutes, followed by 30 cycles of 94° C. for 30 seconds, 50° C. for 30 seconds, and 72° C. for 1 minute. The 30 cycles were followed by incubation at 72° C. for 10 minutes. The PCR product was digested with EcoRI and BamHI and ligated into pPENX-1 and pPENX-2 digested with the same two restriction endonucleases and treated with alkaline phosphatase. The resulting plasmids are designated pPENX1-TNF (SEQ. ID. NO. 20) and pPENX2-TNF (SEQ. ID. NO. 21).

Example 5

Preparation and Transformation of Competent Yeast

K. pastoris was grown in 100 mL YPD to an $OD_{600}$ of 1.0. The cells were pelleted by centrifugation at 3,000× g for 5 minutes and resuspended in 50 mL of 1 M sorbitol, 10 mM Bicine-NaOH (pH 8.3), 3% ethylene glycol, 5% dimethyl sulfoxide. The cells were pelleted by centrifugation at 3,000× g for 5 minutes and resuspended in 2 mL of 1 M sorbitol, 10 mM Bicine-NaOH (pH 8.3), 3% ethylene glycol, 5% dimethyl sulfoxide. pPENX1-TNF and pPENX2-TNF were digested to completion with SacI. Three μg of digested plasmid was incubated with 100 μL of competent K. pastoris at 37° C. for 5 minutes. One mL of 40% polyethylene glycol (MW 1000), 0.2 M Bicine-NaOH (pH 8.3) was added to the transformation mixture and incubated at 37° C. for 1 to 2 hours. The cells were pelleted by centrifugation at 3,000× g for 5 min and resuspended in 1 mL of 10 mM Bicine-NaOH (pH 8.3), 0.15 M NaCl. The cells were again pelleted by centrifugation at 3,000×g for 5 minutes and resuspended in 100 μL of 10 mM Bicine-NaOH (pH 8.3), 0.15 M NaCl. One mL of YPD was added and the cells incubated at 30° C. for 1 hour. The cells were pelleted by centrifugation and resuspended in 100 μL of YPD and the entire 100 μL was plated on YPD agar plates containing G418 (500 μg/mL). The plates were incubated at 30° C. for up to 5 days. Selected colonies were then rechecked to confirm resistance to G418 by streaking on YPD agar medium containing G418 (500 μg/mL).

Example 6

Growth and Expression of TNF in Yeast

1. Testing Transformants for Expression of TNF

To check the level of TNF expression, G418 resistant transformants were grown overnight in shake flasks containing 20 mL of minimal medium (6.7 g/L yeast nitrogen base without amino acids, 1% glycerol, 0.4 μg/L biotin) at 30° C. at 250 rpm in an incubator shaker. The next day, cells were pelleted by centrifugation at 3000×g for 5 minutes. Pellets were resuspended in 2 mL of minimal medium containing methanol. The resuspended cells were used to inoculate 20 mL of minimal medium containing methanol to give an initial $OD_{600}$ of 0.8 to 1.0. The flasks were incubated at 30° C.×250 rpm for up to 4 days. One mL samples of culture were taken at designated times (at least daily) and cells were pelleted by centrifugation in a microcentrifuge and frozen at −20° C. until analysis of TNF production. Each day additional methanol was added to each culture to give 0.5% final concentration. Cell pellets were resuspended in cold 500 μL of 20 mM Tris/Cl (pH 8.0), 40 mM NaCl, 1 mM EDTA. An approximately equal volume of 400–600 micron acid-washed glass beads was added to each pellet in a microcentrifuge tube and vortexed for 4 minutes. The tubes were then centrifuged for 5 minutes and the supernatant transferred to a clean tube. Aliquots of each supernatant were analyzed by Coomassie blue stained SDS-polyacrylamide gel electrophoresis and by Western blotting using anti-human TNF antibody.

2. Production of TNF by High Cell Density Fermentation

A transformant showing the highest level of methanol-induced expression of TNF in the shake flask culture was more extensively analyzed by high cell density fermentation. The transformant was grown in 250 mL of YPD broth at 30° C. for 1–2 days with vigorous agitation, then used to inoculate a 5-liter fermentor (BioFlow 3000; New Brunswick Scientific Co., Inc., Edison, N.J.). The fermentation vessel contained mineral salts (2.3 g $CaSO_4.2H_2O$, 45.5 g $K_2SO_4$, 37.0 g $MgSO_4.7H_2O$, 67 ml $H_3PO_4$, 10.3 g KOH, 100 g glycerol and 12 ml antifoam B (J. T. Baker). Water was added to bring the volume to 2.5 L, and the pH of the medium adjusted to 5.0 using 30% ammonium hydroxide. The fermentor vessel was autoclaved for 35 minutes using a liquid cycle. After cooling 10 ml trace elements (Table 1) were added.

TABLE 1

| | |
|---|---|
| Biotin | 0.2 g |
| Boric acid | 0.02 g |
| Cobalt chloride | 0.5 g |
| Cupric sulfate-5H20 | 6.0 g |
| Ferrous sulfate-7H20 | 65.0 g |
| Manganese sulfate-H20 | 3.0 g |
| Sodium iodide | 0.08 g |
| Sodium molybdate-2H20 | 0.2 g |
| Sulfuric acid | 5.0 ml |
| Zinc chloride | 20.0 g |
| Water | to a final volume of 1 L |

The fermentation was run in three phases, a glycerol batch phase, a glycerol feed phase and finally induction with methanol. Cells were removed from the fermentation vessel at certain time intervals and subsequently analyzed by SDS-polyacrylamide gel electrophoresis. The inoculum was used to seed the fermentor and the fermentation vessel was set to run at 30° C., pH 5.0, and >30% dissolved oxygen. The fermentation was allowed to proceed overnight (23 hr) during which the glycerol was used up by the culture. A yield of 110 g/L of wet cell pellet was obtained during this phase. The second glycerol feed phase was initiated by feeding 50% glycerol containing 10 mL/L trace elements at a rate of 56 mL/hr/liter of culture. A total of 500 ml of glycerol was used during this phase. The cells were allowed to use up the glycerol, as evidenced by an increase in the dissolved oxygen content of the fermentor vessel before induction with methanol was started. A yield of 243 g/L of wet cell pellet was obtained during this second phase. A feed of 100% methanol containing 10 mL/L trace elements was started at a feed rate of 1.5 mL/hr/liter. This rate of feeding was continued for 17 hr and then the feed rate was increased to a rate of 6 mL/hr/L over a 24 hr period. This feed rate was maintained for 31 hr at which time the cells were harvested. A final yield of 350 g/L of wet cell pellet was obtained.

Example 7

Purification and Characterization of TNF Produced in Yeast

1. Purification of TNF from Yeast Cells

The recombinant TNF was produced as a soluble (enzymatically active) protein by K. pastoris. The cell pellet harvested from the fermentation was resuspended in 20 mM Tris-Cl, pH 8.5, 1 mM EDTA. The cells were lysed by passing them twice through a microfluidizer and the particulate material removed by centrifugation. The resulting supernatant was mixed with ammonium sulfate (30% wt/vol) and the insoluble material again removed by centrifugation. The TNF was then diafiltered against 10 volumes of 20 mM Tris-Cl, pH 8.5. The solution was passed over an anion exchange column. The TNF bound to the anion exchange column was eluted with 20 mM Tris-Cl, 150 mM sodium chloride, pH 8.5. This TNF fraction was diafiltered against 10 volumes of 20 mM citrate buffer, pH 5.0. The solution was then passed over a cation exchange column. The TNF bound to the cation exchange column was eluted with 20 mM citrate buffer, 500 mM sodium chloride, pH 5.0. This TNF fraction was diafiltered against 10 volumes of 10 mM sodium phosphate, pH 7.0 and passed over a hydroxyapatite column. The TNF binds to the hydroxyapatite column. Contaminating proteins were eluted with 100 mM sodium phosphate, pH 7.0. TNF was then eluted with 200 mM sodium phosphate, pH 7.0.

2. TNF Cytotoxicity Assay

The TNF purified from the yeast cells was tested for activity by a cytotoxicity assay using L929 cells. TNF-sensitive L929 cells were cultured in D-MEM medium supplemented with 10% fetal bovine serum. One-tenth mL aliquots of L929 cells ($5.0 \times 10^5$ cells/mL) were dispensed into the wells of a 96-well microtiter plates (Corning, Corning, N.Y.), cultured for 18 hours, and exposed to various concentrations of recombinant TNF for 48 hours. To determine the extent of cell death, the cells treated with 0.5 mg/mL MTT (93-[4,5-dimethylthiazol-2-yl]-2,5-diphenyltetrazolium bromide) for four hours, medium removed and cells lysed by the addition of 0.1 mL dimethylsulfoxide. Each plate was analyzed in a microtiter plate reader for color development (OD) at 540 nm (Molecular Devices, Sunnyvale, Calif.). The extent of cell death in the corresponding TNF-treated cell group was calculated as follows: percent cell death=[OD from TNF-treated cells/OD from control cells]×100. The $IC_{50}$ obtained with the TNF purified from the *K. pastoris* was 52 pg/mL which was comparable to the $IC_{50}$ of TNF purified from *Escherichia coli* (133 pg/mL).

Example 8

Secretion of TNF

The leader sequence for the alpha-mating factor from *S. cerevisiae* was ligated into the Eco RI-Kpn I site of pPENX1 and pPENX2 to create pPENX-3 (SEQ ID NO: 22) and pPENX-4 (SEQ ID NO: 23), respectively. pPENX-3 and pPENX-4 allow for the expression of a recombinant gene inserted into these vectors and secretion of the recombinant gene product protein by the host yeast cells into the growth medium.

PCR was used to isolate the alpha-mating factor leader sequence from genomic DNA isolated from *Saccharomyces cerevisiae*. The primers for the PCR had the following sequences:

```
AfacforE 5'-CTCGAATTCACCATGAGATTTCCTTCAATTTTTAC-3', and  (SEQ. ID. NO.24)

AfacrevK: 5'-GAGGGTACCCATATGAGCTTCAGCCTCTCTTTTCTCGAGAGATACCCCTTC-5'  (SEQ. ID. NO.25)
```

The PCR reaction for isolating the alpha-mating factor leader sequence contained 1× Vent PCR buffer (New England Biolabs), 100 ng of purified genomic DNA from *S. cerevisiae*, 0.2 mM dNTPs, 1 µM of each primer, and 1.25 U Vent polymerase (New England Biolabs). The PCR conditions were as follows: 94° C. for 2 minutes, followed by 30 cycles of 94° C. for 30 seconds, 50° C. for 30 seconds, and 72° C. for 1 minute. The 30 cycles were followed by incubation at 72° C. for 10 minutes. The PCR product was purified by agarose gel electrophoresis and digested with Eco RI and Kpn I. pPENX1 and pPENX2 were digested with Eco RI and Kpn I and then treated with alkaline phosphatase. The alpha-mating factor leader sequence was ligated into pPENX-1 and pPENX-2 to create pPENX-3 and pPENX-4, respectively.

The polymerase chain reaction was used to place an Xho I site at the 5' end and a Bam HI site at the 3' end of the mature human TNF coding sequence. The sequences of the primers used for the PCR are shown below.

```
                                                      (SEQ. ID. NO.26)
TNFforX:  5'GTGCTCGAGAAAAGAGTCAGATCATCTTCTCGAACC-3'

(SEQ. ID. NO.27)
TNFrevB:  5'-GAGGGATCCTCACAGGGCAATGATCC-3'
```

The PCR reaction contained IX Vent PCR buffer (New England Biolabs), 10 ng of purified pET-TNF as template, 0.2 mM dNTPs, 1 µM of each primer, and 1.25 U Vent polymerase (New England Biolabs). The PCR conditions were as follows: 94° C. for 2 minutes, followed by 30 cycles of 94° C. for 30 seconds, 50° C. for 30 seconds, and 72° C. for 1 minute. The 30 cycles were followed by incubation at 72° C. for 10 minutes. The PCR product was subcloned into pCR2.1 (Invitrogen). The TNF PCR product was digested out of pCR2.1 with Xho I and Bam HI and ligated into pPENX-4 digested with the same two restriction endonucleases and treated with alkaline phosphatase. The resulting plasmid is designated pPENX4-TNF.

*K. pastoris* was then transformed with SacI digested pPENX4-TNF and plated on YPD agar plates containing G418 as described in Example 5.

To check the level of TNF secretion, G418 resistant transformants were grown overnight in shake flasks containing 20 mL of minimal medium (6.7 g/L yeast nitrogen base without amino acids, 1% glycerol, 0.4 µg/L biotin) at 30° C. at 250 rpm in an incubator shaker. The next day, a sample of the culture was taken and the cells were pelleted by centrifugation. The supernatant was transferred to a clean tube and stored at −20° C. along with the pellets for analysis. The cultures were centrifuged at 3000× g for 5 minutes and the cell pellets were resuspended in 2 mL of minimal medium containing methanol. The resuspended cells were used to inoculate 20 mL of minimal medium containing methanol to give an initial OD600 of 0.8 to 1.0. The flasks were incubated at 30° C.×250 rpm for up to 4 days. One mL samples of culture were taken at designated times (at least daily) and cells pelleted by centrifugation in a microcentrifuge. The cell pellets and supernatants were frozen at −20° C. until analysis of TNF production. Each day additional methanol was added to each culture to give 0.5% final concentration. Aliquots of sample supernatants were analyzed by Coomassie blue stained SDS-polyacrylamide gel electrophoresis and by Western blotting using anti-human TNF antibody. Staining of SDS-polyacrylamide gels shows the presence of a protein band of the correct size for TNF in methanol induced samples that is not seen in preinduction samples. Western blotting using TNF specific antibody indicates the presence of an immunoreactive protein band of the correct size for mature human TNF in induced samples that is not seen in pre-induction samples. These results show that *K. pastoris* can be engineered to secrete a heterologous recombinant protein.

Example 9

Expression of ADI in Different Systems
Expression of ADI in *E. coli*
I. Intracellular Expression For expression of the ADI gene in *E. coli*, the expression vector pQE70 (Qiagen) was used. pQE-70 contains a strong bacteriophage T5 promoter and two lac operator regions adjacent to the promoter. This results in regulation by the LacI repressor protein and expression of the ADI gene is inducible by the addition of IPTG to the culture medium. For insertion of the ADI gene into pQE70, PCR was used to place a SnaB I site at the 5' end of the ADI coding sequence and an Hind III site at the 3' end.

The sequence of the forward primer is:
5'-CTCTACGTATGTCTGTATTTGACAGTAAATTT-AA-3'(SEQ ID NO: 28),
and that of the reverse primer is:
5'-GTGAAGCTTTTACCACTTAACATCTTTACGTG-3'(SEQ ID NO: 29).

The conditions of the PCR were, 94° C.×30 seconds, 50° C.×30 seconds, 72° C.×45 seconds for 30 cycles.

pQE70 was digested with SphI, treated with Klenow fragment to produce blunt ends, then digested with Hind III and Alkaline Phosphatase treated. The ADI PCR product was digested with SnaB I and Hind III and ligated into pQE70. The gene for tetracycline resistance was excised from pBR322 using EcoR I and Ava I, treated with Klenow to produce blunt ends, and ligated into the Bgl I site in the bla (ampicillin resistance) gene in pQE70. The orientation of the tet resistance gene was determined by restriction endonuclease mapping using Bam HI. The resulting plasmid will confer tetracycline resistance, but not ampicillin resistance to transformed *E. coli*. The resulting plasmid containing the ADI and tet resistance genes was designated pPHX-8.

For the expression of ADI, *E. coil* JM101 cells containing pPHX-8 were grown in LB medium containing tetracycline (12.5 µg/mL) to an OD600 of 0.5 to 0.8. Isopropyl-β-D-thiogalactopyranoside (IPTG) was then added to a final concentration of 1 mM to induce the expression of ADI. The cells were grown for an additional 2 hours and then harvested by centrifugation. ADI can be easily seen in cell lysates on SDS-PAGE as a 47,000 MW protein band. ADI makes up about 10% of the total cell protein produced by *E. coli*. The recombinant ADI was expressed in *E. coil* in an inactive form as insoluble inclusion bodies. No ADI enzyme activity was detectable in crude extracts. To obtain active enzyme, the protein must be denatured using 5 M guanidine hydrochloride. The E coli cells were suspended in 10 mM sodium phosphate, pH 7.2 and disrupted with a Microfluidizer. The homogenate was then adjusted to 4% (v/v) with Triton X-100 and centrifuged. The resulting particulate fraction was solubilized in 5 M guanidine hydrochloride in 50 mM sodium phosphate pH 7.2. The recombinant ADI was renatured by rapid dilution into 100 times volume of 10 mM sodium phosphate buffer, pH 7.2. The renatured protein was purified by anion exchange chromatography using Poros HQ resin (Perseptive Biosystems, Boston, Mass.) and a linear gradient of 0–1 M NaCl in 10 mM sodium phosphate pH 7.2. ADI elutes as a sharp peak with approximately 200 mM NaCl. This method results in purified ADI with a specific activity of 19–21 IU/mg of protein.

II. Periplasmic Expression

The coding sequence for ADI was fused to the pelB leader sequence present in pET-22b(+) (Novagen) in order to direct ADI to the *E. coli* periplasmic space. PCR was used to place a Msc I and a Sal I restriction endonuclease sites at the 5' and 3' end of the ADI coding sequence, respectively. The PCR product was digested with Msc I and Sal I and ligated into pET-22b(+) (Novagen). This places the ADI coding sequence in the proper reading frame with the pelB leader sequence. The resulting expression plasmid, pET:ADI, was used to transform BL21(DE3) for expression of ADI. Most of the plasmids isolated from BL21(DE3) transformants did not have the proper structure as determined by restriction mapping (digestion with Xba I+Sal I should produce fragments of 5393, 1086, and 244 bp). A few transformants harbored plasmid that appeared to have the correct structure based on restriction endonuclease digestions and these were used in test inductions to check for ADI expression. Transformants were grown in LB medium containing ampicillin (100 µg/mL) at 37° C. until the OD600 was 0.5 to 0.7 at which time IPTG to 1 mM final concentration was added to the cultures. The cells were incubated for an additional 3 hours and then harvested by centrifugation. Cell lysates were examined for the presence of ADI. No ADI production by any of these transformants was observed with Coomassie blue stained SDS-polyacrylamide gels or by Western blotting.

The pET:ADI expression plasmid was then used to transform BL21 (DE3)pLysS, a strain that more tightly regulates expression when using the pET vectors. In this case transformants were found to harbor plasmids with the proper structure based on restriction endonuclease digestions. Transformants were grown and test inductions carried out as described above, except that cells were grown in LB medium containing ampicillin (100 µg/mL) and chloramphenicol (35 µg/mL). No ADI activity was detected in periplasmic, or whole cell extracts from cells. On Western blots of extracts from induced transformants, two immunoreactive bands, one of 47,000 (native ADI) and a second slightly higher MW band (ADI with the pelB leader still attached), were seen. Coomassie-blue stained SDS-polyacrylamide gels did not show any obvious induction of an ADI size protein, suggesting low levels of ADI production.

Expression of ADI in *Pichia pastoris*

The ADI coding sequence was ligated into the Bam HI-Sna BI site of pPIC3.5. The resulting plasmid, designated pPIC3.5:ADI, was linearized with Sac I and used to transform *P. pastoris* GS115 or *P. pastoris* KM71. His+ transformants were selected by plating on minimal medium without histidine. Test inductions on transformants were performed and cell lysates prepared as described in Example 6. Cell lysates were screened for ADI expression by Western blotting using anti-ADI antibody and ADI enzyme activity assay. Western blotting showed the presence of an immunoreactive protein of 47,000 MW, which is the correct size for ADI. For the detection of ADI activity, the Blood Urea Nitrogen assay was performed. ADI converts arginine into citrulline which reacts with the BUN reagent to produce a pink color. To perform this enzyme assay, a sample was incubated with arginine (10 µM) at 37° C. for 10 min in a phosphate buffer pH 7.2. The Blood Urea Nitrogen Reagent (BUN Reagent, Sigma) was added to the reaction which was then heated to 100° C. for 10 min. The amount of citrulline produced was quantified spectrophotometrically (A595) and compared to a citrulline standard curve. Even though an immunoreactive protein of the correct size was seen in Western blots, no ADI enzyme activity was detectable in any of these lysates.

Expression of ADI in *Komagataella pastoris*

PCR was used to place a Kpn I site at the 5' end and a Bam HI site at the 3' end of the arginine deiminase (ADI) coding sequence. The sequences of the primers used for this are as follows:

```
                                         (SEQ. ID. NO.30)
ADIforK-- 5'-CTCGGTACCATGGCTGTATTTGACAGTAAAT-3'

(SEQ. ID. NO.31)
ADI revB-- 5'-GAGGGATCCTTACCACTTAACATCTTTACG-3'
```

The PCR reaction contained 1× Vent PCR buffer (New England Biolabs), 10 ng of purified pPHX8 DNA, 0.2 mM dNTPs, 1 µM of each primer, and 1.25 U of Vent polymerase (New England Biolabs). The PCR conditions were as follows: 94° C. for 2 minutes, followed by 94° C. for 30 seconds, 50° C. for 30 seconds, and 72° C. for 1 minute for 30 cycles. The 30 cycles were followed by the addition of 1.25 U of Taq polymerase (Stratagene) and incubation at 72° C. for 10 minutes. The PCR produced a single 1250 bp product which was digested with Kpn I and Bam HI. pPENX2 was digested with Kpn I and Bam HI at 37° C. for 1 hour and then treated with calf intestinal alkaline phosphatase at 37° C. for 30 minutes. The ADI PCR product was then ligated into pPENX2. The resulting plasmid, pPENX2:ADI was digested with Sac I and used to transform *K. pastoris* as described in Example 5. Test inductions on transformants were performed and cell lysates prepared as described in Example 6. Cell lysates were screened for ADI expression by Western blotting using anti-ADI antibody and ADI enzyme activity assay. Western blotting showed the presence of an immunoreactive protein of 47,000 MW, which is the correct size for ADI. For the detection of ADI activity, the Blood Urea Nitrogen assay was performed. ADI converts arginine into citrulline which reacts with the BUN reagent to produce a pink color. To perform this enzyme assay, a sample was incubated with arginine (10 µM) at 37° C. for 10 min in a phosphate buffer pH 7.2. The Blood Urea Nitrogen Reagent (BUN Reagent, Sigma) was added to the reaction which was then heated to 100° C. for 10 min. The amount of citrulline produced is quantified spectrophotometrically (A595) and compared to a citrulline standard curve. The enzyme assay for ADI indicated that active ADI was present in the crude lysates.

Each of the patents, patent applications and publications described herein are hereby incorporated by reference in their entirety.

Various modifications of the invention, in addition to those described herein, will be apparent to one skilled in the art in view of the foregoing description. Such modifications are also intended to fall within the scope of patent protection desired and sought.

What is claimed is:

1. An isolated nucleic acid molecule having promoter activity having the nucleotide sequence of SEQ ID NO:1.

2. The isolated promoter of claim 1, wherein the isolated promoter is operably linked to a nucleic acid molecule encoding a desired polypeptide.

3. An expression vector comprising the isolated promoter of claim 1 operably linked to a nucleic acid molecule encoding a desired polypeptide.

4. A method of producing a desired polypeptide comprising the steps of:
   a) introducing the expression vector of claim 3 into a yeast host cell, wherein said host cell is *Komagataella pastoris;*
   b) growing said yeast host cell under conditions for expression of said desired polypeptide; and
   c) recovering said desired polypeptide.

5. A yeast-based expression system for the production of desired polypeptides, said expression system comprising a yeast host cell, wherein said yeast host cell is *Komagataella pastoris*, and an expression vector, said vector comprising a nucleic acid molecule encoding a desired polypeptide, which nucleic acid molecule is operably linked to one or more regulatory regions, and a promoter comprising the sequence of SEQ ID NO:1.

6. The expression system of claim 5 wherein the vector further comprises a nucleic acid molecule encoding a selectable marker.

7. The expression system of claim 5 wherein the vector further comprises a DNA fragment of an autonomously replicating sequence of a methanol assimilating yeast and a nucleic acid molecule encoding a selectable marker.

8. The expression system of claim 5 wherein the desired polypeptide is a deiminase.

9. The expression system of claim 8 wherein the deiminase is arginine deiminase.

10. A method of expressing a desired polypeptide in a yeast host cell, wherein said yeast host cell is *Komagataella pastoris*, comprising transforming said yeast host cell with a vector comprising a promoter, wherein said promoter comprises SEQ ID NO: 1, and a nucleic acid sequence molecule encoding a desired polypeptide, thereby expressing said desired polypeptide.

11. The method of claim 10 wherein said vector is a plasmid.

12. The method of claim 10 wherein said yeast host cell is lysed and said desired polypeptide is recovered from the lysate of said yeast host cell.

13. The method of claim 10 wherein said desired polypeptide is recovered by purifying the culture medium without lysing said yeast host cell.

* * * * *

UNITED STATES PATENT AND TRADEMARK OFFICE
CERTIFICATE OF CORRECTION

PATENT NO.  : 6,645,739 B2
DATED       : November 11, 2003
INVENTOR(S) : Mike A. Clark It is certified that error appears in the above-identified patent and that said Letters Patent is hereby corrected as shown below:

Title page,
Item [73], Assignee, please delete "Pharmacologies," and insert -- Pharmacologics, -- therefor.
Item [56], References Cited, U.S. PATENT DOCUMENTS,
"4,414,329" reference, please insert -- 435/68 -- therefor.
"4,615,974" reference, please insert -- 435/68 -- therefor.
"4,808,537" reference, please insert -- 435/6 -- therefor.
"4,855,231" reference, please insert -- 435/68 -- therefor.
"5,002,876" reference, please insert -- 435/69.5 -- therefor.
"5,641,661" reference, please insert -- 435/161 -- therefor.
"5,707,828" reference, please delete "435/59.1" and insert -- 435/69.1 -- therefor.

Column 4,
Line 9, please delete "*E. coil*" and insert -- *E. coli* -- therefor.

Column 5,
Line 46, please delete "iso-1-cytohrome" and insert -- iso-1-cytochrome -- therefor.

Column 6,
Line 27, please delete "in incorporated" and insert -- is incorporated -- therefor.

Column 10,
Line 48, please delete "phophotransferase" and insert -- phosphotransferase -- therefor.

Column 20,
Line 22, please delete "IX" and insert -- 1X -- therefor.

UNITED STATES PATENT AND TRADEMARK OFFICE
CERTIFICATE OF CORRECTION

PATENT NO.   : 6,645,739 B2
DATED        : November 11, 2003
INVENTOR(S)  : Mike A. Clark It is certified that error appears in the above-identified patent and that said Letters Patent is hereby corrected as shown below:

Column 21,
Line 54, please delete "*E. coil*" and insert -- *E. coli* -- therefor.

Signed and Sealed this

Eighteenth Day of October, 2005

JON W. DUDAS
*Director of the United States Patent and Trademark Office*

SEQUENCE LISTING

<160> NUMBER OF SEQ ID NOS: 31

<210> SEQ ID NO 1
<211> LENGTH: 737
<212> TYPE: DNA
<213> ORGANISM: Komagataella pastoris

<400> SEQUENCE: 1

```
tggagctcgc tcattccaat tccctttgtt aggctactaa gaccacgact ttattagcct    60
gtccattctg gttcctggcg agacttattc ttgtttgttt attttcgaat gcaacaaagc   120
tccgcattac atccgaacat cactttagat gagggctttc tgagtgtggg gtcgaatagt   180
ttcatgttcc cccaatggcc caaaactgac actttaaacg ctgtcttcga acttaatatg   240
gcaaaagcgt gatctcatcc aagacgaact aagtttggtt cgttgaaatg ctaacggcca   300
gttggtcaaa aagaaacttc caaaagtcgg catatcgttt gtcttgtttg gtattcatag   360
acgaatgctc aagaatattc tcattaatgc ttagcgcagt ctctgtatcg cttctggacc   420
ccggtgcagt tgtgccgaaa cgcaaatggg gaaacacccg cttttcggat gattatgcat   480
tgtctccaca ttgtatgctt ccaagattct ggtgggaata ctactgatag cctaacgttc   540
atgatcaata tcaaactgtt ctaaccccta cttgaactgc aatatataaa caggaggaaa   600
cttcccagtc gaaaaccttc tttcatcatc attattagct tactttcata attgtgactg   660
gttccaattg acaagctttt gattctaacg acttttaacg acaatttgag aagatcaaaa   720
acaactaatt attcgaa                                                  737
```

<210> SEQ ID NO 2

<211> LENGTH: 22
<212> TYPE: DNA
<213> ORGANISM: Artificial Sequence
<220> FEATURE:
<223> OTHER INFORMATION: Primer

<400> SEQUENCE: 2
ggagctcgct cattccaatt cc                                          22

<210> SEQ ID NO 3
<211> LENGTH: 17
<212> TYPE: DNA
<213> ORGANISM: Artificial Sequence
<220> FEATURE:
<223> OTHER INFORMATION: Primer

<400> SEQUENCE: 3
gtgtggtcac cgaagaa                                                17

<210> SEQ ID NO 4
<211> LENGTH: 30
<212> TYPE: DNA
<213> ORGANISM: Artificial Sequence
<220> FEATURE:
<223> OTHER INFORMATION: Primer

<400> SEQUENCE: 4
gtgaagcttt caagaggatg tcagaatgcc                                  30

<210> SEQ ID NO 5
<211> LENGTH: 33
<212> TYPE: DNA
<213> ORGANISM: Artificial Sequence
<220> FEATURE:
<223> OTHER INFORMATION: Primer

<400> SEQUENCE: 5
cacacatgtg tgggaaatac cttgaaaaac atc                              33

<210> SEQ ID NO 6
<211> LENGTH: 1957
<212> TYPE: DNA
<213> ORGANISM: Artificial Sequence
<220> FEATURE:
<223> OTHER INFORMATION: PCR Product

<400> SEQUENCE: 6
tggagctcgc tcattccaat tccctttgtt aggctactaa gaccacgact ttattagcct   60
gtccattctg gttcctggcg agacttattc ttgtttgttt attttcgaat gcaacaaagc  120
tccgcattac atccgaacat cactttagat gagggctttc tgagtgtggg gtcgaatagt  180
ttcatgttcc cccaatggcc caaaactgac actttaaacg ctgtcttcga acttaatatg  240
gcaaaagcgt gatctcatcc aagacgaact aagtttggtt cgttgaaatg ctaacggcca  300
gttggtcaaa agaaacttc caaagtcgg catatcgttt gtcttgtttg gtattcatag     360
acgaatgctc aagaatattc tcattaatgc ttagcgcagt ctctgtatcg cttctggacc  420
ccggtgcagt tgtgccgaaa cgcaaatggg gaaacacccg cttttcggat gattatgcat  480
tgtctccaca ttgtatgctt ccaagattct ggtgggaata ctactgatag cctaacgttc  540
atgatcaata tcaaactgtt ctaaccccta cttgaactgc aatatataaa caggaggaaa  600
cttcccagtc gaaaaccttc tttcatcatc attattagct tactttcata attgtgactg  660
gttccaattg acaagctttt gattctaacg acttttaacg acaatttgag aagatcaaaa  720

-continued

```
acaactaatt attcgaaacg atggctatcc ctgaagagtt tgatatcctt gttttaggtg      780
gtggatccag tggatcctgt attgccggaa gattggccaa cttggaccac tccttgaaag      840
ttggtcttat cgaggcaggt gagaacaacc tcaacaaccc atgggtttac cttccaggta      900
tttacccaag aaacatgaag ttggactcca agactgcatc cttctacact tctaacccct      960
ctcctcactt gaacggtaga agagctattg ttccatgtgc taacgtcttg ggtggtggtt     1020
cttccattaa cttcatgatg tacaccagag gttctgcttc tgattatgac gacttccaag     1080
ccgagggctg gaaaaccaag gacttgcttc cattgatgaa aaagaccgag acctaccaaa     1140
gagcttgcaa caaccctgac attcacgggt tcgaaggtcc aatcaaggtt tctttcggta     1200
actacaccta cccagtttgc caggacttct tgagagcttc tgaatcccaa ggtattccat     1260
acgttgacga cttggaagac ttggttactg ctcacggtgc tgaacactgg ctgaaatgga     1320
tcaacagaga cactggtcgt cgttccgact ccgctcatgc atttgtccac tctactatga     1380
gaaaccacga caacttgtac ttgatttgta acacaaaggt tgacaagatt attgtcgaag     1440
acggaagagc tgctgctgtt agaactgttc aagcaagcc tttgaaccca agaagccaa      1500 gtcacaagat ctaccgtgct agaaagcaaa tcgttttgtc ttgtggtacc atctcatctc     1560
ctttggttct gcaaagatcc ggtttcggtg acccaatcaa gttgagagcc gctggtgtta     1620
agcctttggt caacttgcct ggtgtcggaa gaaacttcca agaccactac tgtttcttca     1680
gtccttacag aatcaagcct cagtacgaat ctttcgatga cttcgtgcgt ggtgatgctg     1740
agatccaaaa gagagttttc gaccaatggt acgccaatgg tactggtcct cttgccacta     1800
acggtatcga agccggtgtc aagattagac aacaccaga ggaactgtct caaatggacg      1860
aatctttcca agagggttac agagaatact ttgaggacaa gccagacagg ccagttatgc     1920
actactccat tattgctggt ttcttcggtg accacac                              1957
```

<210> SEQ ID NO 7
<211> LENGTH: 216
<212> TYPE: DNA
<213> ORGANISM: Pichia pastoris

<400> SEQUENCE: 7

```
tcaagaggat gtcagaatgc catttgcctg agagatgcag gcttcatttt tgatacttt       60 ttatttgtaa cctatatagt ataggatttt ttttgtcatt tgtttcttc tcgtacgagc      120 ttgctcctga tcagcctatc tcgcagctga tgaatatctt gtggtagggg tttgggaaaa     180
tcattcgagt ttgatgtttt tcaaggtatt tcccac                               216
```

<210> SEQ ID NO 8
<211> LENGTH: 26
<212> TYPE: DNA
<213> ORGANISM: Artificial Sequence
<220> FEATURE:
<223> OTHER INFORMATION: Primer

<400> SEQUENCE: 8

```
gtgactagta tgattgaaca agatgg                                           26
```

<210> SEQ ID NO 9
<211> LENGTH: 29
<212> TYPE: DNA
<213> ORGANISM: Artificial Sequence
<220> FEATURE:
<223> OTHER INFORMATION: Primer -continued

```
<400> SEQUENCE: 9
cacgcggccg ctcagaagaa ctcgtcaag                                            29

<210> SEQ ID NO 10
<211> LENGTH: 27
<212> TYPE: DNA
<213> ORGANISM: Artificial Sequence
<220> FEATURE:
<223> OTHER INFORMATION: Primer

<400> SEQUENCE: 10
gtgaatattc ccacacacca tagcttc                                              27

<210> SEQ ID NO 11
<211> LENGTH: 27
<212> TYPE: DNA
<213> ORGANISM: Artificial Sequence
<220> FEATURE:
<223> OTHER INFORMATION: Primer

<400> SEQUENCE: 11
cacactagta aacttagatt agattgc                                              27

<210> SEQ ID NO 12
<211> LENGTH: 30
<212> TYPE: DNA
<213> ORGANISM: Artificial Sequence
<220> FEATURE:
<223> OTHER INFORMATION: Primer

<400> SEQUENCE: 12
gtggcggccg cggccccttt tcctttgtcg                                           30

<210> SEQ ID NO 13
<211> LENGTH: 35
<212> TYPE: DNA
<213> ORGANISM: Artificial Sequence
<220> FEATURE:
<223> OTHER INFORMATION: Primer

<400> SEQUENCE: 13
ctcaatatta agcttgcaaa ttaaagcctt cgagc                                     35

<210> SEQ ID NO 14
<211> LENGTH: 29
<212> TYPE: DNA
<213> ORGANISM: Artificial Sequence
<220> FEATURE:
<223> OTHER INFORMATION: Primer

<400> SEQUENCE: 14
gtgcatatgt ggagctcgct cattccaat                                            29

<210> SEQ ID NO 15
<211> LENGTH: 32
<212> TYPE: DNA
<213> ORGANISM: Artificial Sequence
<220> FEATURE:
<223> OTHER INFORMATION: Primer

<400> SEQUENCE: 15
cacgaattct tcgaataatt agttgttttt tg                                        32

<210> SEQ ID NO 16
<211> LENGTH: 4573
```

<212> TYPE: DNA
<213> ORGANISM: Artificial Sequence
<220> FEATURE:
<223> OTHER INFORMATION: Plasmid

<400> SEQUENCE: 16

| | | | | | |
|---|---|---|---|---|---|
| tcgcgcgttt | cggtgatgac | ggtgaaaacc | tctgacacat | gcagctcccg | gagacggtca | 60 |
| cagcttgtct | gtaagcggat | gccgggagca | gacaagcccg | tcagggcgcg | tcagcgggtg | 120 |
| ttggcgggtg | tcggggctgg | cttaactatg | cggcatcaga | gcagattgta | ctgagagtgc | 180 |
| accaattccc | acacaccata | gcttcaaaat | gtttctactc | cttttttact | cttccagatt | 240 |
| ttctcggact | ccgcgcatcg | ccgtaccact | caaaacacc | caagcacagc | atactaaatt | 300 |
| ttccctcttt | cttcctctag | ggtgtcgtta | attacccgta | ctaaaggttt | ggaaaagaaa | 360 |
| aaagagaccg | cctcgtttct | ttttcttcgt | cgaaaaggc | aataaaaatt | tttatcacgt | 420 |
| ttcttttct | tgaaattttt | tttttagtt | tttttctctt | tcagtgacct | ccattgatat | 480 |
| ttaagttaat | aaacggtctt | caatttctca | agtttcagtt | tcatttttct | tgttctatta | 540 |
| caactttttt | tacttcttgt | tcattagaaa | gaaagcatag | caatctaatc | taagtttact | 600 |
| agtatgattg | aacaagatgg | attgcacgca | ggttctccgg | ccgcttgggt | ggagaggcta | 660 |
| ttcggctatg | actgggcaca | acagacaatc | ggctgctctg | atgccgccgt | gttccggctg | 720 |
| tcagcgcagg | ggcgcccggt | tctttttgtc | aagaccgacc | tgtccggtgc | cctgaatgaa | 780 |
| ctgcaggacg | aggcagcgcg | gctatcgtgg | ctggccacga | cgggcgttcc | ttgcgcagct | 840 |
| gtgctcgacg | ttgtcactga | agcgggaagg | gactggctgc | tattgggcga | agtgccgggg | 900 |
| caggatctcc | tgtcatctca | ccttgctcct | gccgagaaag | tatccatcat | ggctgatgca | 960 |
| atgcggcggc | tgcatacgct | tgatccggct | acctgcccat | tcgaccacca | agcgaaacat | 1020 |
| cgcatcgagc | gagcacgtac | tcggatggaa | gccggtcttg | tcgatcagga | tgatctggac | 1080 |
| gaagagcatc | aggggctcgc | gccagccgaa | ctgttcgcca | ggctcaaggc | gcgcatgccc | 1140 |
| gacggcgagg | atctcgtcgt | gacccatggc | gatgcctgct | tgccgaatat | catggtggaa | 1200 |
| aatggccgct | tttctggatt | catcgactgt | ggccggctgg | gtgtggcgga | ccgctatcag | 1260 |
| gacatagcgt | tggctacccg | tgatattgct | gaagagcttg | gcggcgaatg | ggctgaccgc | 1320 |
| ttcctcgtgc | tttacggtat | cgccgctccc | gattcgcagc | gcatcgcctt | ctatcgcctt | 1380 |
| cttgacgagt | tcttctgagc | ggcgcggcc | ccttttcctt | tgtcgatatc | atgtaattag | 1440 |
| ttatgtcacg | cttacattca | cgccctcccc | ccacatccgc | tctaaccgaa | aaggaaggag | 1500 |
| ttagacaacc | tgaagtctag | gtccctattt | attttttat | agttatgtta | gtattaagaa | 1560 |
| cgttatttat | atttcaaatt | tttctttttt | ttctgtacag | acgcgtgtac | gcatgtaaca | 1620 |
| ttatactgaa | aaccttgctt | gagaaggttt | tgggacgctc | gaaggcttta | atttgcaagc | 1680 |
| ttaattgtgg | agctcgctca | ttccaattcc | ctttgttagg | ctactaagac | cacgacttta | 1740 |
| ttagcctgtc | cattctggtt | cctggcgaga | cttattcttg | tttgtttatt | ttcgaatgca | 1800 |
| acaaagctcc | gcattacatc | cgaacatcac | tttagatgag | ggctttctga | gtgtgggtc | 1860 |
| gaatagtttc | atgttccccc | aatggcccaa | aactgacact | taaacgctg | tcttcgaact | 1920 |
| taatatggca | aaagcgtgat | ctcatccaag | acgaactaag | tttggttcgt | tgaaatgcta | 1980 |
| acggccagtt | ggtcaaaaag | aaacttccaa | agtcggcat | atcgtttgtc | ttgtttggta | 2040 |
| ttcatagacg | aatgctcaag | aatattctca | ttaatgctta | gcgcagtctc | tgtatcgctt | 2100 |
| ctggaccccg | gtgcagttgt | gccgaaacgc | aaatgggaa | acacccgctt | ttcggatgat | 2160 |

-continued

```
tatgcattgt ctccacattg tatgcttcca agattctggt gggaatacta ctgtatagcct    2220
aacgttcatg atcaatatca aactgttcta acccctactt gaactgcaat atataaacag    2280
gaggaaactt cccagtcgaa aaccttcttt catcatcatt attagcttac tttcataatt    2340
gtgactggtt ccaattgaca agcttttgat tctaacgtct tttaacgaca acttagaaga    2400
tcaaaaacaa ctaattattc gaagaattcg cggtacccgg ggatcctcta gagtcgacct    2460
gcaggcatgc aagctttcaa gaggatgtca gaatgccatt tgcctgagag atgcaggctt    2520
catttttgat acttttttat ttgtaaccta tatagtatag dattttttttt gtcattttgt    2580
ttcttctcgt acgagcttgc tcctgatcag cctatctcgc agctgatgaa tatcttgtgg    2640
tagggggtttg ggaaaatcat tcgagtttga tgttttttcaa ggtatttccc acacatgtga    2700
gcaaaaggcc agcaaaaggc caggaaccgt aaaaaggccg cgttgctggc gttttttccat    2760
aggctccgcc cccctgacga gcatcacaaa aatcgacgct caagtcagag gtggcgaaac    2820
ccgacaggac tataaagata ccaggcgttt ccccctggaa gctccctcgt gcgctctcct    2880
gttccgaccc tgccgcttac cggatacctg tccgcctttc tcccttcggg aagcgtggcg    2940
ctttctcata gctcacgctg taggtatctc agttcggtgt aggtcgttcg ctccaagctg    3000
ggctgtgtgc acgaaccccc cgttcagccc gaccgctgcg ccttatccgg taactatcgt    3060
cttgagtcca acccggtaag acacgactta tcgccactgg cagcagccac tggtaacagg    3120
attagcagag cgaggtatgt aggcggtgct acagagttct tgaagtggtg cctaactac     3180
ggctacacta aaggacagt atttggtatc tgcgctctgc tgaagccagt taccttcgga    3240
aaaagagttg gtagctcttg atccggcaaa caaaccaccg ctggtagcgg tggttttttt    3300
gtttgcaagc agcagattac gcgcagaaaa aaaggatctc aagaagatcc tttgatcttt    3360
tctacggggt ctgacgctca gtggaacgaa aactcacgtt aagggatttt ggtcatgaga    3420
ttatcaaaaa ggatcttcac ctagatcctt ttaaattaaa aatgaagttt taaatcaatc    3480
taaagtatat atgagtaaac ttggtctgac agttaccaat gcttaatcag tgaggcacct    3540
atctcagcga tctgtctatt tcgttcatcc atagttgcct gactccccgt cgtgtagata    3600
actacgatac gggagggctt accatctggc cccagtgctg caatgatacc gcgagaccca    3660
cgctcaccgg ctccagattt atcagcaata accagccag ccggaagggc cgagcgcaga    3720
agtggtcctg caactttatc cgcctccatc cagtctatta attgttgccg ggaagctaga    3780
gtaagtagtt cgccagttaa tagtttgcgc aacgttgttg ccattgctac aggcatcgtg    3840
gtgtcacgct cgtcgtttgg tatggcttca ttcagctccg gttcccaacg atcaaggcga    3900
gttacatgat cccccatgtt gtgcaaaaaa gcggttagct ccttcggtcc tccgatcgtt    3960
gtcagaagta agttggccgc agtgttatca ctcatggtta tggcagcact gcataattct    4020
cttactgtca tgccatccgt aagatgcttt tctgtgactg gtgagtactc aaccaagtca    4080
ttctgagaat agtgtatgcg cgaccgagt tgctcttgcc cggcgtcaat acgggataat    4140
accgcgccac atagcagaac tttaaaagtc ctcatcattg gaaaacgttc ttcggggcga    4200
aaactctcaa ggatcttacc gctgttgaga tccagttcga tgtaacccac tcgtgcaccc    4260
aactgatctt cagcatcttt tactttcacc agcgtttctg ggtgagcaaa acaggaagg    4320
caaaatgccg caaaaaaggg aataagggcg acacggaaat gttgaatact catactcttc    4380
cttttttcaat attattgaag catttatcag ggttattgtc tcatgagcgg atacatattt    4440
gaatgtattt agaaaaataa acaaataggg gttccgcgca catttccccg aaaagtgcca    4500
cctgacgtct aagaaaccat tattatcatg acattaacct ataaaaatag gcgtatcacg    4560
``` aggcccttte gtc                                                     4573

<210> SEQ ID NO 17
<211> LENGTH: 4573
<212> TYPE: DNA
<213> ORGANISM: Artificial Sequence
<220> FEATURE:
<223> OTHER INFORMATION: Plasmid

<400> SEQUENCE: 17

| | | | | | |
|---|---|---|---|---|---|
| tcgcgcgttt | cggtgatgac | ggtgaaaacc | tctgacacat | gcagctcccg | gagacggtca | 60 |
| cagcttgtct | gtaagcggat | gccgggagca | gacaagcccg | tcagggcgcg | tcagcgggtg | 120 |
| ttggcgggtg | tcgggctgg | cttaactatg | cggcatcaga | gcagattgta | ctgagagtgc | 180 |
| accaattaag | cttgcaaatt | aaagccttcg | agcgtcccaa | aaccttctca | agcaaggttt | 240 |
| tcagtataat | gttacatgcg | tacacgcgtc | tgtacagaaa | aaaagaaaa | atttgaaata | 300 |
| taaataacgt | tcttaatact | aacataacta | taaaaaaata | aatagggacc | tagacttcag | 360 |
| gttgtctaac | tccttccttt | tcggttagag | cggatgtggg | gggagggcgt | gaatgtaagc | 420 |
| gtgacataac | taattacatg | atatcgacaa | aggaaaaggg | gccgcggccg | ctcagaagaa | 480 |
| ctcgtcaaga | aggcgataga | aggcgatgcg | ctgcgaatcg | ggagcggcga | taccgtaaag | 540 |
| cacgaggaag | cggtcagccc | attcgccgcc | aagctcttca | gcaatatcac | gggtagccaa | 600 |
| cgctatgtcc | tgatagcggt | ccgccacacc | cagccggcca | cagtcgatga | atccagaaaa | 660 |
| gcggccattt | tccaccatga | tattcggcaa | gcaggcatcg | ccatgggtca | cgacgagatc | 720 |
| ctcgccgtcg | ggcatgcgcg | ccttgagcct | ggcgaacagt | tcggctggcg | cgagcccctg | 780 |
| atgctcttcg | tccagatcat | cctgatcgac | aagaccggct | tccatccgag | tacgtgctcg | 840 |
| ctcgatgcga | tgtttcgctt | ggtggtcgaa | tgggcaggta | gccggatcaa | gcgtatgcag | 900 |
| ccgccgcatt | gcatcagcca | tgatggatac | tttctcggca | ggagcaaggt | gagatgacag | 960 |
| gagatcctgc | cccggcactt | cgcccaatag | cagccagtcc | cttcccgctt | cagtgacaac | 1020 |
| gtcgagcaca | gctgcgcaag | gaacgcccgt | cgtggccagc | cacgatagcc | gcgctgcctc | 1080 |
| gtcctgcagt | tcattcaggg | caccggacag | gtcggtcttg | acaaaaagaa | ccgggcgccc | 1140 |
| ctgcgctgac | agccggaaca | cggcggcatc | agagcagccg | attgtctgtt | gtgcccagtc | 1200 |
| atagccgaat | agcctctcca | cccaagcggc | cggagaacct | gcgtgcaatc | catcttgttc | 1260 |
| aatcatacta | gtaaacttag | attagattgc | tatgctttct | ttctaatgaa | caagaagtaa | 1320 |
| aaaaagttgt | aatagaacaa | gaaaatgaa | actgaaactt | gagaaattga | agaccgttta | 1380 |
| ttaacttaaa | tatcaatgga | ggtcactgaa | agagaaaaaa | actaaaaaaa | aaatttcaa | 1440 |
| gaaaaagaaa | cgtgataaaa | attttattg | ccttttcga | cgaagaaaaa | gaaacgaggc | 1500 |
| ggtctctttt | ttcttttcca | aacctttagt | acgggtaatt | aacgacaccc | tagaggaaga | 1560 |
| aagagggaaa | atttagtatg | ctgtgcttgg | gtgttttgaa | gtggtacggc | gatgcgcgga | 1620 |
| gtccgagaaa | atctggaaga | gtaaaaaagg | agtagaaaca | ttttgaagct | atggtgtgtg | 1680 |
| ggaattgtgg | agctcgctca | ttccaattcc | ctttgttagg | ctactaagac | cacgacttta | 1740 |
| ttagcctgtc | cattctggtt | cctggcgaga | cttattcttg | tttgtttatt | ttcgaatgca | 1800 |
| acaaagctcc | gcattacatc | cgaacatcac | tttagatgag | ggctttctga | gtgtggggtc | 1860 |
| gaatagtttc | atgttccccc | aatggcccaa | aactgacact | ttaaacgctg | tcttcgaact | 1920 |
| taatatggca | aaagcgtgat | ctcatccaag | acgaactaag | tttggttcgt | tgaaatgcta | 1980 |

-continued

| | | |
|---|---|---|
| acggccagtt ggtcaaaaag aaacttccaa aagtcggcat atcgtttgtc ttgtttggta | 2040 |
| ttcatagacg aatgctcaag aatattctca ttaatgctta gcgcagtctc tgtatcgctt | 2100 |
| ctggaccccg gtgcagttgt gccgaaacgc aaatggggaa acacccgctt tcggatgat | 2160 |
| tatgcattgt ctccacattg tatgcttcca agattctggt gggaatacta ctgatagcct | 2220 |
| aacgttcatg atcaatatca aactgttcta acccctactt gaactgcaat atataaacag | 2280 |
| gaggaaactt cccagtcgaa aaccttcttt catcatcatt attagcttac tttcataatt | 2340 |
| gtgactggtt ccaattgaca agcttttgat tctaacgtct tttaacgaca acttagaaga | 2400 |
| tcaaaaacaa ctaattattc gaagaattcg cggtacccgg ggatcctcta gagtcgacct | 2460 |
| gcaggcatgc aagctttcaa gaggatgtca gaatgccatt tgcctgagag atgcaggctt | 2520 |
| catttttgat acttttttat ttgtaaccta tatagtatag gattttttt gtcattttgt | 2580 |
| ttcttctcgt acgagcttgc tcctgatcag cctatctcgc agctgatgaa tatcttgtgg | 2640 |
| tagggttttg ggaaaatcat tcgagtttga tgttttcaa ggtatttccc acacatgtga | 2700 |
| gcaaaaggcc agcaaaaggc caggaaccgt aaaaaggccg cgttgctggc gttttttccat | 2760 |
| aggctccgcc cccctgacga gcatcacaaa aatcgacgct caagtcagag gtggcgaaac | 2820 |
| ccgacaggac tataaagata ccaggcgttt ccccctggaa gctccctcgt gcgctctcct | 2880 |
| gttccgaccc tgccgcttac cggatacctg tccgcctttc tcccttcggg aagcgtggcg | 2940 |
| ctttctcata gctcacgctg taggtatctc agttcggtgt aggtcgttcg ctccaagctg | 3000 |
| ggctgtgtgc acgaaccccc cgttcagccc gaccgctgcg ccttatccgg taactatcgt | 3060 |
| cttgagtcca acccggtaag acacgactta tcgccactgg cagcagccac tggtaacagg | 3120 |
| attagcagag cgaggtatgt aggcggtgct acagagttct tgaagtggtg gcctaactac | 3180 |
| ggctacacta aaggacagt atttggtatc tgcgctctgc tgaagccagt taccttcgga | 3240 |
| aaaagagttg gtagctcttg atccggcaaa caaaccaccg ctggtagcgg tggttttttt | 3300 |
| gtttgcaagc agcagattac gcgcagaaaa aaaggatctc aagaagatcc tttgatcttt | 3360 |
| tctacggggt ctgacgctca gtggaacgaa aactcacgtt aagggatttt ggtcatgaga | 3420 |
| ttatcaaaaa ggatcttcac ctagatcctt ttaaattaaa aatgaagttt taaatcaatc | 3480 |
| taaagtatat atgagtaaac ttggtctgac agttaccaat gcttaatcag tgaggcacct | 3540 |
| atctcagcga tctgtctatt tcgttcatcc atagttgcct gactccccgt cgtgtagata | 3600 |
| actacgatac gggagggctt accatctggc cccagtgctg caatgatacc gcgagaccca | 3660 |
| cgctcaccgg ctccagattt atcagcaata aaccagccag ccggaagggc cgagcgcaga | 3720 |
| agtggtcctg caactttatc cgcctccatc cagtctatta attgttgccg ggaagctaga | 3780 |
| gtaagtagtt cgccagttaa tagtttgcgc aacgttgttg ccattgctac aggcatcgtg | 3840 |
| gtgtcacgct cgtcgtttgg tatggcttca ttcagctccg gttcccaacg atcaaggcga | 3900 |
| gttacatgat cccccatgtt gtgcaaaaaa gcggttagct ccttcggtcc tccgatcgtt | 3960 |
| gtcagaagta agttggccgc agtgttatca ctcatggtta tggcagcact gcataattct | 4020 |
| cttactgtca tgccatccgt aagatgcttt tctgtgactg gtgagtactc aaccaagtca | 4080 |
| ttctgagaat agtgtatgcg gcgaccgagt tgctcttgcc cggcgtcaat acgggataat | 4140 |
| accgcgccac atagcagaac tttaaaagtg ctcatcattg gaaaacgttc ttcggggcga | 4200 |
| aaactctcaa ggatcttacc gctgttgaga tccagttcga tgtaacccac tcgtgcaccc | 4260 |
| aactgatctt cagcatcttt tactttcacc agcgtttctg ggtgagcaaa aacaggaagg | 4320 |
| caaaatgccg caaaaaaggg aataagggcg acacggaaat gttgaatact catactcttc | 4380 |

```
cttttttcaat attattgaag catttatcag ggttattgtc tcatgagcgg atacatattt    4440
gaatgtattt agaaaaataa acaaataggg gttccgcgca catttccccg aaaagtgcca    4500
cctgacgtct aagaaaccat tattatcatg acattaacct ataaaaatag gcgtatcacg    4560
aggccctttc gtc                                                       4573
```

<210> SEQ ID NO 18
<211> LENGTH: 29
<212> TYPE: DNA
<213> ORGANISM: Artificial Sequence
<220> FEATURE:
<223> OTHER INFORMATION: Primer

<400> SEQUENCE: 18

```
ctcgaattca ccatggtcag atcatcttc                                        29
```

<210> SEQ ID NO 19
<211> LENGTH: 26
<212> TYPE: DNA
<213> ORGANISM: Artificial Sequence
<220> FEATURE:
<223> OTHER INFORMATION: Primer

<400> SEQUENCE: 19

```
gagggatcct cacagggcaa tgatcc                                           26
```

<210> SEQ ID NO 20
<211> LENGTH: 5042
<212> TYPE: DNA
<213> ORGANISM: Artificial Sequence
<220> FEATURE:
<223> OTHER INFORMATION: Plasmid

<400> SEQUENCE: 20

```
tcgcgcgttt cggtgatgac ggtgaaaacc tctgacacat gcagctcccg gagacggtca      60
cagcttgtct gtaagcggat gccgggagca gacaagcccg tcagggcgcg tcagcgggtg     120
ttggcgggtg tcgggctgg cttaactatg cggcatcaga gcagattgta ctgagagtgc     180
accaattccc acacaccata gcttcaaaat gtttctactc cttttttact cttccagatt     240
ttctcggact ccgcgcatcg ccgtaccact tcaaaacacc caagcacagc atactaaatt     300
tcccctcttt cttcctctag ggtgtcgtta attacccgta ctaaggtttt ggaaagaaa     360 aaagagaccg cctcgtttct ttttcttcgt cgaaaaaggc aataaaaatt tttatcacgt     420 ttcttttttct tgaaattttt ttttttagtt tttttctctt tcagtgacct ccattgatat     480
ttaagttaat aaacggtctt caatttctca gtttcagtt tcattttct tgttctatta     540 caacttttttt tacttcttgt tcattagaaa gaaagcatag caatctaatc taagtttact     600
agtatgattg aacaagatgg attgcacgca ggttctccgg ccgcttgggt ggagaggcta     660
ttcggctatg actgggcaca acagacaatc ggctgctctg atgccgccgt gttccggctg     720
tcagcgcagg ggcgcccggt tctttttgtc aagaccgacc tgtccggtgc cctgaatgaa     780
ctgcaggacg aggcagcgcg gctatcgtgg ctggccacga cgggcgttcc ttgcgcagct     840
gtgctcgacg ttgtcactga agcgggaagg gactggctgc tattgggcga agtgccgggg     900
caggatctcc tgtcatctca ccttgctcct gccgagaaag tatccatcat ggctgatgca     960
atgcggcggc tgcatacgct tgatccggct acctgcccat tcgaccacca agcgaaacat     1020
cgcatcgagc gagcacgtac tcggatggaa gccggtcttg tcgatcagga tgatctggac    1080
```

```
gaagagcatc agggctcgc gccagccgaa ctgttcgcca ggctcaaggc gcgcatgccc    1140
gacggcgagg atctcgtcgt gacccatggc gatgcctgct tgccgaatat catggtggaa    1200
aatggccgct tttctggatt catcgactgt ggccggctgg gtgtggcgga ccgctatcag    1260
gacatagcgt tggctacccg tgatattgct gaagagcttg gcggcgaatg ggctgaccgc    1320
ttcctcgtgc tttacggtat cgccgctccc gattcgcagc gcatcgcctt ctatcgcctt    1380
cttgacgagt tcttctgagc ggccgcggcc ccttttcctt tgtcgatatc atgtaattag    1440
ttatgtcacg cttacattca cgccctcccc ccacatccgc tctaaccgaa aggaaggag    1500
ttagacaacc tgaagtctag gtccctattt attttttat agttatgtta gtattaagaa    1560
cgttatttat atttcaaatt tttctttttt ttctgtacag acgcgtgtac gcatgtaaca    1620
ttatactgaa aaccttgctt gagaaggttt tgggacgctc gaaggcttta atttgcaagc    1680
ttaattgtgg agctcgctca ttccaattcc ctttgttagg ctactaagac cacgactttta    1740
ttagcctgtc cattctggtt cctggcgaga cttattcttg tttgtttatt ttcgaatgca    1800
acaaagctcc gcattacatc cgaacatcac tttagatgag ggctttctga gtgtggggtc    1860
gaatagtttc atgttccccc aatggcccaa aactgacact ttaaacgctg tcttcgaact    1920
taatatggca aaagcgtgat ctcatccaag acgaactaag tttggttcgt tgaaatgcta    1980
acggccagtt ggtcaaaaag aaacttccaa aagtcggcat atcgtttgtc ttgtttggta    2040
ttcatagacg aatgctcaag aatattctca ttaatgctta gcgcagtctc tgtatcgctt    2100
ctggaccccg gtgcagttgt gccgaaacgc aaatggggaa acacccgctt ttcggatgat    2160
tatgcattgt ctccacattg tatgcttcca agattctggt gggaatacta ctgatagcct    2220
aacgttcatg atcaatatca aactgttcta acccctactt gaactgcaat atataaacag    2280
gaggaaactt cccagtcgaa aaccttcttt catcatcatt attagcttac tttcataatt    2340
gtgactggtt ccaattgaca agcttttgat tctaacgtct tttaacgaca acttagaaga    2400
tcaaaaacaa ctaattattc gaagaattca ccatggtcag atcatcttct cgaaccccga    2460
gtgacaagcc tgtagcccat gttgtagcaa accctcaagc tgaggggcag ctccagtggc    2520
tgaaccgccg ggccaatgcc ctcctggcca atggcgtgga gctgagagat aaccagctgg    2580
tggtgccatc agagggcctg tacctcatct actcccaggt cctcttcaag ggccaaggct    2640
gcccctccac ccatgtgctc ctcacccaca ccatcagccg catcgccgtc tcctaccaga    2700
ccaaggtcaa cctcctctct gccatcaaga gcccctgcca gagggagacc ccagagggg    2760
ctgaggccaa gccctggtat gagcccatct atctgggagg ggtcttccag ctggagaagg    2820
gtgaccgact cagcgctgag atcaatcggc ccgactatct cgactttgcc gagtctgggc    2880
aggtctactt tgggatcatt gccctgtgag atcctctag agtcgacctg caggcatgca    2940
agctttcaag aggatgtcag aatgccattt gcctgagaga tgcaggcttc attttttgata    3000
cttttttatt tgtaacctat atagtatagg attttttttg tcattttgtt tcttctcgta    3060
cgagcttgct cctgatcagc ctatctcgca gctgatgaat atcttgtggt aggggtttgg    3120
gaaaatcatt cgagtttgat gtttttcaag gtatttccca cacatgtgag caaaaggcca    3180
gcaaaaggcc aggaaccgta aaaaggccgc gttgctggcg ttttccata ggctccgccc    3240
ccctgacgag catcacaaaa atcgacgctc aagtcagagg tggcgaaacc cgacaggact    3300
ataaagatac caggcgtttc ccctggaag ctccctcgtg cgctctcctg ttccgaccct    3360
gccgcttacc ggatacctgt ccgcctttct cccttcggga agcgtggcgc tttctcatag    3420
ctcacgctgt aggtatctca gttcggtgta ggtcgttcgc tccaagctgg gctgtgtgca    3480
```

-continued

```
cgaacccccc gttcagcccg accgctgcgc cttatccggt aactatcgtc ttgagtccaa    3540
cccggtaaga cacgacttat cgccactggc agcagccact ggtaacagga ttagcagagc    3600
gaggtatgta ggcggtgcta cagagttctt gaagtggtgg cctaactacg gctacactag    3660
aaggacagta tttggtatct gcgctctgct gaagccagtt accttcggaa aaagagttgg    3720
tagctcttga tccggcaaac aaaccaccgc tggtagcggt ggtttttttg tttgcaagca    3780
gcagattacg cgcagaaaaa aaggatctca agaagatcct ttgatctttt ctacggggtc    3840
tgacgctcag tggaacgaaa actcacgtta agggattttg gtcatgagat tatcaaaaag    3900
gatcttcacc tagatccttt taaattaaaa atgaagtttt aaatcaatct aaagtatata    3960
tgagtaaact tggtctgaca gttaccaatg cttaatcagt gaggcaccta tctcagcgat    4020
ctgtctattt cgttcatcca tagttgcctg actccccgtc gtgtagataa ctacgatacg    4080
ggagggctta ccatctggcc ccagtgctgc aatgataccg cgagacccac gctcaccggc    4140
tccagattta tcagcaataa accagccagc cggaagggcc gagcgcagaa gtggtcctgc    4200
aactttatcc gcctccatcc agtctattaa ttgttgccgg gaagctagag taagtagttc    4260
gccagttaat agtttgcgca acgttgttgc cattgctaca ggcatcgtgg tgtcacgctc    4320
gtcgtttggt atggcttcat tcagctccgg ttcccaacga tcaaggcgag ttacatgatc    4380
ccccatgttg tgcaaaaaag cggttagctc cttcggtcct ccgatcgttg tcagaagtaa    4440
gttggccgca gtgttatcac tcatggttat ggcagcactg cataattctc ttactgtcat    4500
gccatccgta agatgctttt ctgtgactgg tgagtactca accaagtcat tctgagaata    4560
gtgtatgcgg cgaccgagtt gctcttgccc ggcgtcaata cgggataata ccgcgccaca    4620
tagcagaact ttaaaagtgc tcatcattgg aaaacgttct cggggcgaaa actctcaag    4680
gatcttaccg ctgttgagat ccagttcgat gtaaccact cgtgcaccca actgatcttc    4740
agcatctttt actttcacca gcgtttctgg gtgagcaaaa acaggaaggc aaaatgccgc    4800
aaaaaaggga ataagggcga cacggaaatg ttgaatactc atactcttcc ttttcaata    4860
ttattgaagc atttatcagg gttattgtct catgagcgga tacatatttg aatgtattta    4920
gaaaaataaa caataggggg ttccgcgcac atttccccga aaagtgccac ctgacgtcta    4980
agaaaccatt attatcatga cattaaccta taaaaatagg cgtatcacga ggccctttcg    5040
tc                                                                   5042
```

<210> SEQ ID NO 21
<211> LENGTH: 5042
<212> TYPE: DNA
<213> ORGANISM: Artificial Sequence
<220> FEATURE:
<223> OTHER INFORMATION: Plasmid

<400> SEQUENCE: 21

```
tcgcgcgttt cggtgatgac ggtgaaaacc tctgacacat gcagctcccg gagacggtca      60
cagcttgtct gtaagcggat gccgggagca gacaagcccg tcagggcgcg tcagcgggtg     120
ttggcgggtg tcggggctgg cttaactatg cggcatcaga gcagattgta ctgagagtgc     180
accaattaag cttgcaaatt aaagccttcg agcgtcccaa aaccttctca gcaaggttt     240
tcagtataat gttacatgcg tacacgcgtc tgtacagaaa aaaagaaaa atttgaaata     300
taaataacgt tcttaatact aacataacta aaaaaaata aatagggacc tagacttcag     360
gttgtctaac tccttccttt tcggttagag cggatgtggg gggagggcgt gaatgtaagc     420
```

-continued

```
gtgacataac taattacatg atatcgacaa aggaaaaggg gccgcggccg ctcagaagaa    480
ctcgtcaaga aggcgataga aggcgatgcg ctgcgaatcg ggagcggcga taccgtaaag    540
cacgaggaag cggtcagccc attcgccgcc aagctcttca gcaatatcac gggtagccaa    600
cgctatgtcc tgatagcggt ccgccacacc cagccggcca cagtcgatga atccagaaaa    660
gcggccattt tccaccatga tattcggcaa gcaggcatcg ccatgggtca cgacgagatc    720
ctcgccgtcg ggcatgcgcg ccttgagcct ggcgaacagt tcggctggcg cgagcccctg    780
atgctcttcg tccagatcat cctgatcgac aagaccggct tccatccgag tacgtgctcg    840
ctcgatgcga tgtttcgctt ggtggtcgaa tgggcaggta gccggatcaa gcgtatgcag    900
ccgccgcatt gcatcagcca tgatggatac tttctcggca ggagcaaggt gagatgacag    960
gagatcctgc cccggcactt cgcccaatag cagccagtcc cttcccgctt cagtgacaac   1020
gtcgagcaca gctgcgcaag gaacgcccgt cgtggccagc cacgatagcc gcgctgcctc   1080
gtcctgcagt tcattcaggg caccggacag gtcggtcttg acaaaaagaa ccgggcgccc   1140
ctgcgctgac agccggaaca cggcggcatc agagcagccg attgtctgtt gtcccagtc    1200 atagccgaat agcctctcca cccaagcggc cggagaacct gcgtgcaatc catcttgttc   1260
aatcatacta gtaaacttag attagattgc tatgcttcct ttctaatgaa caagaagtaa   1320
aaaaagttgt aatagaacaa gaaaaatgaa actgaaactt gagaaattga agaccgttta   1380
ttaacttaaa tatcaatgga ggtcactgaa agagaaaaaa actaaaaaaa aaatttcaa    1440 gaaaaagaaa cgtgataaaa attttttattg cctttttcga cgaagaaaaa gaaacgaggc   1500
ggtctctttt ttcttttcca aacctttagt acgggtaatt aacgacaccc tagaggaaga   1560
aagagggaaa atttagtatg ctgtgcttgg gtgttttgaa gtggtacggc gatgcgcgga   1620
gtccgagaaa atctggaaga gtaaaaaagg agtagaaaca ttttgaagct atggtgtgtg   1680
ggaattgtgg agctcgctca ttccaattcc ctttgttagg ctactaagac cacgacttta   1740
ttagcctgtc cattctggtt cctggcgaga cttattcttg tttgtttatt ttcgaatgca   1800
acaaagctcc gcattacatc cgaacatcac tttagatgag ggctttctga gtgtggggtc   1860
gaatagtttc atgttccccc aatggcccaa aactgacact ttaaacgctg tcttcgaact   1920
taatatggca aaagcgtgat ctcatccaag acgaactaag tttggttcgt tgaaatgcta   1980
acggccagtt ggtcaaaaag aaacttccaa aagtcggcat atcgtttgtc ttgtttggta   2040
ttcatagacg aatgctcaag aatattctca ttaatgctta gcgcagtctc tgtatcgctt   2100
ctggaccccg gtgcagttgt gccgaaacgc aaatgggaa acacccgctt tcggatgat    2160 tatgcattgt ctccacattg tatgcttcca agattctggt gggaatacta ctgatagcct   2220
aacgttcatg atcaatatca aactgttcta accctactt gaactgcaat atataaacag    2280
gaggaaactt cccagtcgaa aaccttcttt catcatcatt attagcttac tttcataatt   2340
gtgactggtt ccaattgaca agcttttgat tctaacgtct tttaacgaca acttagaaga   2400
tcaaaaacaa ctaattattc gaagaattca ccatggtcag atcatcttct cgaacccga    2460 gtgacaagcc tgtagcccat gttgtagcaa accctcaagc tgagggcag ctccagtggc    2520 tgaaccgccg ggccaatgcc ctcctggcca atggcgtgga gctgagagat aaccagctgg   2580
tggtgccatc agagggcctg tacctcatct actcccaggt cctcttcaag ggccaaggct   2640
gcccctccac ccatgtgctc ctcacccaca ccatcagccg catcgccgtc tcctaccaga   2700
ccaaggtcaa cctcctctct gccatcaaga gcccctgcca gagggagacc ccagagggg    2760 ctgaggccaa gccctggtat gagcccatct atctgggagg ggtcttccag ctggagaagg   2820
```

-continued

```
gtgaccgact cagcgctgag atcaatcggc ccgactatct cgactttgcc gagtctgggc    2880
aggtctactt tgggatcatt gccctgtgag gatcctctag agtcgacctg caggcatgca    2940
agctttcaag aggatgtcag aatgccattt gcctgagaga tgcaggcttc attttttgata   3000 cttttttatt tgtaacctat atagtatagg attttttttg tcattttgtt tcttctcgta    3060
cgagcttgct cctgatcagc ctatctcgca gctgatgaat atcttgtggt aggggtttgg    3120
gaaaatcatt cgagtttgat gttttttcaag gtatttccca cacatgtgag caaaaggcca    3180
gcaaaaggcc aggaaccgta aaaaggccgc gttgctggcg ttttttccata ggctccgccc    3240 ccctgacgag catcacaaaa atcgacgctc aagtcagagg tggcgaaacc cgacaggact    3300
ataaagatac caggcgtttc ccctggaag ctccctcgtg cgctctcctg ttccgaccct     3360
gccgcttacc ggatacctgt ccgcctttct cccttcggga agcgtggcgc tttctcatag    3420
ctcacgctgt aggtatctca gttcggtgta ggtcgttcgc tccaagctgg gctgtgtgca    3480 cgaaccccc gttcagcccg accgctgcgc cttatccggt aactatcgtc ttgagtccaa     3540
cccggtaaga cacgacttat cgccactggc agcagccact ggtaacagga ttagcagagc    3600
gaggtatgta ggcggtgcta cagagttctt gaagtggtgg cctaactacg gctacactag    3660
aaggacagta tttggtatct gcgctctgct gaagccagtt accttcggaa aaagagttgg    3720
tagctcttga tccggcaaac aaaccaccgc tggtagcggt ggttttttg tttgcaagca     3780 gcagattacg cgcagaaaaa aaggatctca agaagatcct ttgatctttt ctacggggtc    3840
tgacgctcag tggaacgaaa actcacgtta agggattttg gtcatgagat tatcaaaaag    3900
gatcttcacc tagatccttt taaattaaaa atgaagtttt aaatcaatct aaagtatata    3960
tgagtaaact tggtctgaca gttaccaatg cttaatcagt gaggcaccta tctcagcgat    4020
ctgtctattt cgttcatcca tagttgcctg actccccgtc gtgtagataa ctacgatacg    4080
ggagggctta ccatctggcc ccagtgctgc aatgataccg cgagacccac gctcaccggc    4140
tccagattta tcagcaataa accagccagc cggaagggcc gagcgcagaa gtggtcctgc    4200
aactttatcc gcctccatcc agtctattaa ttgttgccgg gaagctagag taagtagttc    4260
gccagttaat agtttgcgca acgttgttgc cattgctaca ggcatcgtgg tgtcacgctc    4320
gtcgtttggt atggcttcat tcagctccgg ttcccaacga tcaaggcgag ttacatgatc    4380
ccccatgttg tgcaaaaaag cggttagctc cttcggtcct ccgatcgttg tcagaagtaa    4440
gttggccgca gtgttatcac tcatggttat ggcagcactg cataattctc ttactgtcat    4500
gccatccgta agatgctttt ctgtgactgg tgagtactca accaagtcat tctgagaata    4560
gtgtatgcgg cgaccgagtt gctcttgccc ggcgtcaata cgggataata ccgcgccaca    4620
tagcagaact ttaaaagtgc tcatcattgg aaaacgttct cggggcgaa aactctcaag     4680 gatcttaccg ctgttgagat ccagttcgat gtaacccact cgtgcaccca actgatcttc    4740
agcatctttt actttcacca gcgtttctgg gtgagcaaaa acaggaaggc aaaatgccgc    4800
aaaaaaggga ataagggcga cacgaaatg ttgaatactc atactcttcc ttttcaata     4860 ttattgaagc atttatcagg gttattgtct catgagcgga tacatatttg aatgtattta    4920
gaaaaataaa caaatagggg ttccgcgcac atttccccga aaagtgccac ctgacgtcta    4980
agaaaccatt attatcatga cattaaccta taaaaatagg cgtatcacga ggcccttttcg   5040 tc                                                                   5042
```

<210> SEQ ID NO 22

<211> LENGTH: 4847
<212> TYPE: DNA
<213> ORGANISM: Artificial Sequence
<220> FEATURE:
<223> OTHER INFORMATION: Plasmid

<400> SEQUENCE: 22

| | | | | | |
|---|---|---|---|---|---|
| tcgcgcgttt | cggtgatgac | ggtgaaaacc | tctgacacat | gcagctcccg | gagacggtca | 60 |
| cagcttgtct | gtaagcggat | gccgggagca | gacaagcccg | tcagggcgcg | tcagcgggtg | 120 |
| ttggcgggtg | tcgggctgg | cttaactatg | cggcatcaga | gcagattgta | ctgagagtgc | 180 |
| accaattccc | acacaccata | gcttcaaaat | gtttctactc | cttttttact | cttccagatt | 240 |
| ttctcggact | ccgcgcatcg | ccgtaccact | caaaacacc | caagcacagc | atactaaatt | 300 |
| ttccctctttt | cttcctctag | ggtgtcgtta | attacccgta | ctaaaggttt | ggaaaagaaa | 360 |
| aaagagaccg | cctcgtttct | tttcttcgt | cgaaaaaggc | aataaaaatt | tttatcacgt | 420 |
| ttctttttct | tgaaattttt | tttttagtt | tttttctctt | tcagtgacct | ccattgatat | 480 |
| ttaagttaat | aaacggtctt | caattctca | agtttcagtt | tcattttct | tgttctatta | 540 |
| caacttttt | tacttcttgt | tcattagaaa | gaaagcatag | caatctaatc | taagtttact | 600 |
| agtatgattg | aacaagatgg | attgcacgca | ggttctccgg | ccgcttgggt | ggagaggcta | 660 |
| ttcggctatg | actgggcaca | acagacaatc | ggctgctctg | atgccgccgt | gttccggctg | 720 |
| tcagcgcagg | ggcgcccggt | tctttttgtc | aagaccgacc | tgtccggtgc | cctgaatgaa | 780 |
| ctgcaggacg | aggcagcgcg | gctatcgtgg | ctggccacga | cgggcgttcc | ttgcgcagct | 840 |
| gtgctcgacg | ttgtcactga | agcgggaagg | gactggctgc | tattgggcga | agtgccgggg | 900 |
| caggatctcc | tgtcatctca | ccttgctcct | gccgagaaag | tatccatcat | ggctgatgca | 960 |
| atgcggcggc | tgcatacgct | tgatccggct | acctgcccat | tcgaccacca | agcgaaacat | 1020 |
| cgcatcgagc | gagcacgtac | tcggatggaa | gccggtcttg | tcgatcagga | tgatctggac | 1080 |
| gaagagcatc | agggggctcgc | gccagccgaa | ctgttcgcca | ggctcaaggc | gcgcatgccc | 1140 |
| gacggcgagg | atctcgtcgt | gacccatggc | gatgcctgct | tgccgaatat | catggtggaa | 1200 |
| aatggccgct | tttctggatt | catcgactgt | ggccggctgg | gtgtggcgga | ccgctatcag | 1260 |
| gacatagcgt | tggctacccg | tgatattgct | gaagagcttg | gcggcgaatg | ggctgaccgc | 1320 |
| ttcctcgtgc | tttacggtat | cgccgctccc | gattcgcagc | gcatcgcctt | ctatcgcctt | 1380 |
| cttgacgagt | tcttctgagc | ggcgcgggcc | ccttttcctt | tgtcgatatc | atgtaattag | 1440 |
| ttatgtcacg | cttacattca | cgccctcccc | ccacatccgc | tctaaccgaa | aaggaaggag | 1500 |
| ttagacaacc | tgaagtctag | gtccctattt | attttttat | agttatgtta | gtattaagaa | 1560 |
| cgttatttat | atttcaaatt | tttctttttt | ttctgtacag | acgcgtgtac | gcatgtaaca | 1620 |
| ttatactgaa | aaccttgctt | gagaaggttt | tgggacgctc | gaaggcttta | atttgcaagc | 1680 |
| ttaattgtgg | agctcgctca | ttccaattcc | ctttgttagg | ctactaagac | cacgacttta | 1740 |
| ttagcctgtc | cattctggtt | cctggcgaga | cttattcttg | tttgtttatt | ttcgaatgca | 1800 |
| acaaagctcc | gcattacatc | cgaacatcac | tttagatgag | ggctttctga | gtgtgggtc | 1860 |
| gaatagtttc | atgttccccc | aatggcccaa | aactgacact | ttaaacgctg | tcttcgaact | 1920 |
| taatatggca | aaagcgtgat | ctcatccaag | acgaactaag | tttggttcgt | tgaaatgcta | 1980 |
| acggccagtt | ggtcaaaaag | aaacttccaa | agtcggcat | atcgtttgtc | ttgtttggta | 2040 |
| ttcatagacg | aatgctcaag | aatattctca | ttaatgctta | gcgcagtctc | tgtatcgctt | 2100 |
| ctggaccccg | gtgcagttgt | gccgaaacgc | aaatggggaa | acaccgcgtt | tcggatgat | 2160 |

-continued

```
tatgcattgt ctccacattg tatgcttcca agattctggt gggaatacta ctgatagcct      2220
aacgttcatg atcaatatca aactgttcta acccctactt gaactgcaat atataaacag      2280
gaggaaactt cccagtcgaa aaccttcttt catcatcatt attagcttac tttcataatt      2340
gtgactggtt ccaattgaca agcttttgat tctaacgtct tttaacgaca acttagaaga      2400
tcaaaaacaa ctaattattc gaagaattca ccatgagatt tccttcaatt tttactgcag      2460
ttttattcgc agcatcctcc gcattagctg ctccagtcaa cactacaaca gaagatgaaa      2520
cggcacaaat tccggctgaa gctgtcatcg gttactcaga tttagaaggg gatttcgatg      2580
ttgctgtttt gccatttttcc aacagcacaa ataacgggtt attgtttata aatactacta      2640
ttgccagcat tgctgctaaa gaagaagggg tatctctcga gaaagagag gctgaagctc      2700 atatgggtac ccggggatcc tctagagtcg acctgcaggc atgcaagctt caagaggat       2760 gtcagaatgc catttgcctg agagatgcag gcttcatttt tgatactttt ttatttgtaa      2820
cctatatagt ataggatttt ttttgtcatt ttgtttcttc tcgtacgagc ttgctcctga      2880
tcagcctatc tcgcagctga tgaatatctt gtggtagggg tttgggaaaa tcattcgagt      2940
ttgatgtttt tcaaggtatt tcccacacat gtgagcaaaa ggccagcaaa aggccaggaa      3000
ccgtaaaaag gccgcgttgc tggcgttttt ccataggctc cgcccccctg acgagcatca      3060
caaaaatcga cgctcaagtc agaggtggcg aaacccgaca ggactataaa gataccaggc      3120
gtttccccct ggaagctccc tcgtgcgctc tcctgttccg accctgccgc ttaccggata      3180
cctgtccgcc tttctccctt cgggaagcgt ggcgctttct catagctcac gctgtaggta      3240
tctcagttcg gtgtaggtcg ttcgctccaa gctgggctgt gtgcacgaac cccccgttca      3300
gcccgaccgc tgcgccttat ccggtaacta tcgtcttgag tccaacccgg taagacacga      3360
cttatcgcca ctggcagcag ccactggtaa caggattagc agagcgaggt atgtaggcgg      3420
tgctacagag ttcttgaagt ggtggcctaa ctacggctac actagaagga cagtatttgg      3480
tatctgcgct ctgctgaagc cagttacctt cggaaaaaga gttggtagct cttgatccgg      3540
caaacaaacc accgctggta gcggtggttt ttttgtttgc aagcagcaga ttacgcgcag      3600
aaaaaaagga tctcaagaag atcctttgat cttttctacg gggtctgacg ctcagtggaa      3660
cgaaaactca cgttaaggga ttttggtcat gagattatca aaaaggatct tcacctagat      3720
ccttttaaat taaaaatgaa gttttaaatc aatctaaagt atatatgagt aaacttggtc      3780
tgacagttac caatgcttaa tcagtgaggc acctatctca gcgatctgtc tatttcgttc      3840
atccatagtt gcctgactcc ccgtcgtgta gataactacg atacgggagg gcttaccatc      3900
tggccccagt gctgcaatga taccgcgaga cccacgctca ccggctccag atttatcagc      3960
aataaaccag ccagccggaa gggccgagcg cagaagtggt cctgcaactt tatccgcctc      4020
catccagtct attaattgtt gccgggaagc tagagtaagt agttcgccag ttaatagttt      4080
gcgcaacgtt gttgccattg ctacaggcat cgtggtgtca cgctcgtcgt ttggtatggc      4140
ttcattcagc tccggttccc aacgatcaag gcgagttaca tgatccccca tgttgtgcaa      4200
aaaagcggtt agctccttcg gtcctccgat cgttgtcaga agtaagttgg ccgcagtgtt      4260
atcactcatg gttatggcag cactgcataa ttctcttact gtcatgccat ccgtaagatg      4320
cttttctgtg actggtgagt actcaaccaa gtcattctga gaatagtgta tgcggcgacc      4380
gagttgctct tgcccggcgt caatacggga taataccgcg ccacatagca gaactttaaa      4440
agtgctcatc attggaaaac gttcttcggg gcgaaaactc tcaaggatct taccgctgtt      4500
```

| | |
|---|---:|
| gagatccagt tcgatgtaac ccactcgtgc acccaactga tcttcagcat cttttacttt | 4560 |
| caccagcgtt tctgggtgag caaaaacagg aaggcaaaat gccgcaaaaa agggaataag | 4620 |
| ggcgacacgg aaatgttgaa tactcatact cttccttttt caatattatt gaagcattta | 4680 |
| tcagggttat tgtctcatga gcggatacat atttgaatgt atttagaaaa ataaacaaat | 4740 |
| aggggttccg cgcacatttc cccgaaaagt gccacctgac gtctaagaaa ccattattat | 4800 |
| catgacatta acctataaaa ataggcgtat cacgaggccc tttcgtc | 4847 |

<210> SEQ ID NO 23
<211> LENGTH: 4836
<212> TYPE: DNA
<213> ORGANISM: Artificial Sequence
<220> FEATURE:
<223> OTHER INFORMATION: Plasmid

<400> SEQUENCE: 23

| | |
|---|---:|
| tcgcgcgttt cggtgatgac ggtgaaaacc tctgacacat gcagctcccg gagacggtca | 60 |
| cagcttgtct gtaagcggat gccgggagca gacaagcccg tcaggcgcg tcagcgggtg | 120 |
| ttggcgggtg tcgggctgg cttaactatg cggcatcaga gcagattgta ctgagagtgc | 180 |
| accaattaag cttgcaaatt aaagccttcg agcgtcccaa aaccttctca agcaaggttt | 240 |
| tcagtataat gttacatgcg tacacgcgtc tgtacagaaa aaaagaaaa atttgaaata | 300 |
| taaataacgt tcttaatact aacataacta taaaaaaata aatagggacc tagacttcag | 360 |
| gttgtctaac tccttccttt tcggttagag cggatgtggg gggagggcgt gaatgtaagc | 420 |
| gtgacataac taattacatg atatcgacaa aggaaaggg gccgcggccg ctcagaagaa | 480 |
| ctcgtcaaga aggcgataga aggcgatgcg ctgcgaatcg ggagcggcga taccgtaaag | 540 |
| cacgaggaag cggtcagccc attcgccgcc aagctcttca gcaatatcac gggtagccaa | 600 |
| cgctatgtcc tgatagcggt ccgccacacc cagccggcca cagtcgatga atccagaaaa | 660 |
| gcggccattt tccaccatga tattcggcaa gcaggcatcg ccatgggtca cgacgagatc | 720 |
| ctcgccgtcg gcatgcgcg ccttgagcct ggcgaacagt tcggctggcg cgagcccctg | 780 |
| atgctcttcg tccagatcat cctgatcgac aagaccggct tccatccgag tacgtgctcg | 840 |
| ctcgatgcga tgtttcgctt ggtggtcgaa tgggcaggta gccggatcaa gcgtatgcag | 900 |
| ccgccgcatt gcatcagcca tgatggatac tttctcggca ggagcaaggt gagatgacag | 960 |
| gagatcctgc cccggcactt cgcccaatag cagccagtcc cttcccgctt cagtgacaac | 1020 |
| gtcgagcaca gctgcgcaag gaacgcccgt cgtggccagc cacgatagcc gcgctgcctc | 1080 |
| gtcctgcagt tcattcaggg caccggacag gtcggtcttg acaaaaagaa ccgggcgccc | 1140 |
| ctgcgctgac agccggaaca cggcggcatc agagcagccg attgtctgtt gtgcccagtc | 1200 |
| atagccgaat agcctctcca cccaagcggc cggagaacct gcgtgcaatc catcttgttc | 1260 |
| aatcatacta gtaaacttag attagattgc tatgctttct ttctaatgaa caagaagtaa | 1320 |
| aaaaagttgt aatagaacaa gaaaatgaa actgaaactt gagaaattga agaccgttta | 1380 |
| ttaacttaaa tatcaatgga ggtcactgaa agagaaaaaa actaaaaaaa aaatttcaa | 1440 |
| gaaaagaaa cgtgataaaa attttttattg cctttttcga cgaagaaaaa gaaacgaggc | 1500 |
| ggtctctttt ttcttttcca aacctttagt acgggtaatt aacgacaccc tagaggaaga | 1560 |
| aagagggaaa atttagtatg ctgtgcttgg gtgttttgaa gtggtacggc gatgcgcgga | 1620 |
| gtccgagaaa atctggaaga gtaaaaaagg agtagaaaca ttttgaagct atggtgtgtg | 1680 |
| ggaattgtgg agctcgctca ttccaattcc ctttgttagg ctactaagac cacgactta | 1740 |

-continued

```
ttagcctgtc cattctggtt cctggcgaga cttattcttg tttgtttatt ttcgaatgca    1800
acaaagctcc gcattacatc cgaacatcac tttagatgag ggctttctga gtgtggggtc    1860
gaatagtttc atgttccccc aatggcccaa aactgacact ttaaacgctg tcttcgaact    1920
taatatggca aaagcgtgat ctcatccaag acgaactaag tttggttcgt tgaaatgcta    1980
acggccagtt ggtcaaaaag aaacttccaa aagtcggcat atcgtttgtc ttgtttggta    2040
ttcatagacg aatgctcaag aatattctca ttaatgctta gcgcagtctc tgtatcgctt    2100
ctggaccccg gtgcagttgt gccgaaacgc aaatggggaa acacccgctt tcggatgat    2160 tatgcattgt ctccacattg tatgcttcca agattctggt gggaatacta ctgatagcct    2220
aacgttcatg atcaatatca aactgttcta acccctactt gaactgcaat atataaacag    2280
gaggaaactt cccagtcgaa aaccttcttt catcatcatt attagcttac tttcataatt    2340
gtgactggtt ccaattgaca agcttttgat tctaacgtct tttaacgaca acttagaaga    2400
tcaaaaacaa ctaattattc gaagaattca ccatgagatt tccttcaatt tttactgcag    2460
ttttattcgc agcatcctcc gcattagctg ctccagtcaa cactacaaca gaagatgaaa    2520
cggcacaaat tccggctgaa gctgtcatcg gttactcaga tttagaaggg gatttcgatg    2580
ttgctgtttt gccattttcc aacagcacaa ataacgggtt attgtttata aatactacta    2640
ttgccagcat tgctgctaaa gaagaagggg tatctctcga gaaagagag gctgaagctc    2700 atatgggtac ccggggatcc tctagagtcg acctgcaggc atgcaagctt caagaggat    2760 gtcagaatgc catttgcctg agagatgcag gcttcatttt tgatactttt ttatttgtaa    2820
cctatatagt ataggatttt ttttgtcatt ttgtttcttc tcgtacgagc ttgctcctga    2880
tcagcctatc tcgcagctga tgaatatctt gtggtagggg tttgggaaaa tcattcgagt    2940
ttgatgtttt tcaaggtatt tcccacacat gtgagcaaaa ggccagcaaa aggccaggaa    3000
ccgtaaaaag gccgcgttgc tggcgttttt ccataggctc cgcccccctg acgagcatca    3060
caaaaatcga cgctcaagtc agaggtggcg aaacccgaca ggactataaa gataccaggc    3120
gtttccccct ggaagctccc tcgtgcgctc tcctgttccg accctgccgc ttaccggata    3180
cctgtccgcc tttctccctt cgggaagcgt ggcgctttct catagctcac gctgtaggta    3240
tctcagttcg gtgtaggtcg ttcgctccaa gctgggctgt gtgcacgaac cccccgttca    3300
gcccgaccgc tgcgccttat ccggtaacta tcgtcttgag tccaacccgg taagacacga    3360
cttatcgcca ctggcagcag ccactggtaa caggattagc agagcgaggt atgtaggcgg    3420
tgctacagag ttcttgaagt ggtggcctaa ctacggctac actagaagga cagtatttgg    3480
tatctgcgct ctgctgaagc cagttacctt cggaaaaaga gttggtagct cttgatccgg    3540
caaacaaacc accgctggta gcggtggttt ttttgtttgc aagcagcaga ttacgcgcag    3600
aaaaaaagga tctcaagaag atcctttgat cttttctacg gggtctgacg ctcagtggaa    3660
cgaaaactca cgttaaggga ttttggtcat gagattatca aaaggatct tcacctagat    3720 ccttttaaat taaaaatgaa gttttaaatc aatctaaagt atatatgagt aaacttggtc    3780
tgacagttac caatgcttaa tcagtgaggc acctatctca gcgatctgtc tatttcgttc    3840
atccatagtt gcctgactcc ccgtcgtgta gataactacg atacgggagg gcttaccatc    3900
tggccccagt gctgcaatga taccgcgaga cccacgctca ccggctccag atttatcagc    3960
aataaaccag ccagccggaa gggccgagcg cagaagtggt cctgcaactt tatccgcctc    4020
catccagtct attaattgtt gccgggaagc tagagtaagt agttcgccag ttaatagttt    4080
```

```
gcgcaacgtt gttgccattg ctacaggcat cgtggtgtca cgctcgtcgt ttggtatggc    4140
ttcattcagc tccggttccc aacgatcaag gcgagttaca tgatccccca tgttgtgcaa    4200
aaaagcggtt agctccttcg gtcctccgat cgttgtcaga agtaagttgg ccgcagtgtt    4260
atcactcatg gttatggcag cactgcataa ttctcttact gtcatgccat ccgtaagatg    4320
cttttctgtg actggtgagt actcaaccaa gtcattctga gaatagtgta tgcggcgacc    4380
gagttgctct tgcccggcgt caatacggga taataccgcg ccacatagca gaactttaaa    4440
agtgctcatc attggaaaac gttcttcggg gcgaaaactc tcaaggatct taccgctgtt    4500
gagatccagt tcgatgtaac ccactcgtgc acccaactga tcttcagcat cttttacttt    4560
caccagcgtt tctgggtgag caaaaacagg aaggcaaaat gccgcaaaaa agggaataag    4620
ggcgacacgg aaatgttgaa tactcatact cttcctttt caatattatt gaagcattta    4680
tcagggttat tgtctcatga gcggatacat atttgaatgt atttagaaaa ataaacaaat    4740
aggggttccg cgcacatttc cccgaaaagt gccacctgac gtctaagaaa ccattattat    4800
catgacatta acctataaaa ataggcgtat cacgag                              4836
```

<210> SEQ ID NO 24
<211> LENGTH: 35
<212> TYPE: DNA
<213> ORGANISM: Artificial Sequence
<220> FEATURE:
<223> OTHER INFORMATION: Primer

<400> SEQUENCE: 24
ctcgaattca ccatgagatt tccttcaatt tttac                               35

<210> SEQ ID NO 25
<211> LENGTH: 51
<212> TYPE: DNA
<213> ORGANISM: Artificial Sequence
<220> FEATURE:
<223> OTHER INFORMATION: Primer

<400> SEQUENCE: 25
gagggtaccc atatgagctt cagcctctct tttctcgaga gataccccctt c            51

<210> SEQ ID NO 26
<211> LENGTH: 36
<212> TYPE: DNA
<213> ORGANISM: Artificial Sequence
<220> FEATURE:
<223> OTHER INFORMATION: Primer

<400> SEQUENCE: 26
gtgctcgaga aaagagtcag atcatcttct cgaacc                              36

<210> SEQ ID NO 27
<211> LENGTH: 26
<212> TYPE: DNA
<213> ORGANISM: Artificial Sequence
<220> FEATURE:
<223> OTHER INFORMATION: Primer

<400> SEQUENCE: 27
gagggatcct cacagggcaa tgatcc                                         26

<210> SEQ ID NO 28
<211> LENGTH: 34
<212> TYPE: DNA
<213> ORGANISM: Artificial Sequence -continued

```
<220> FEATURE:
<223> OTHER INFORMATION: Primer

<400> SEQUENCE: 28
ctctacgtat gtctgtattt gacagtaaat ttaa                              34

<210> SEQ ID NO 29
<211> LENGTH: 32
<212> TYPE: DNA
<213> ORGANISM: Artificial Sequence
<220> FEATURE:
<223> OTHER INFORMATION: Primer

<400> SEQUENCE: 29
gtgaagcttt taccacttaa catctttacg tg                                32

<210> SEQ ID NO 30
<211> LENGTH: 31
<212> TYPE: DNA
<213> ORGANISM: Artificial Sequence
<220> FEATURE:
<223> OTHER INFORMATION: Primer

<400> SEQUENCE: 30
ctcggtacca tggctgtatt tgacagtaaa t                                 31

<210> SEQ ID NO 31
<211> LENGTH: 30
<212> TYPE: DNA
<213> ORGANISM: Artificial Sequence
<220> FEATURE:
<223> OTHER INFORMATION: Primer

<400> SEQUENCE: 31
gagggatcct taccacttaa catctttacg                                   30
```